(12) United States Patent
Li et al.

(10) Patent No.: US 7,699,979 B2
(45) Date of Patent: Apr. 20, 2010

(54) SEPARATION SYSTEM AND EFFICIENT CAPTURE OF CONTAMINANTS USING MAGNETIC NANOPARTICLES

(75) Inventors: Yanbin Li, Fayetteville, AR (US); Madhukar Varshney, Fayetteville, AR (US); Zunzhang Ye, Fayetteville, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 984 days.

(21) Appl. No.: 11/328,808

(22) Filed: Jan. 9, 2006

(65) Prior Publication Data

US 2007/0114181 A1 May 24, 2007

Related U.S. Application Data

(60) Provisional application No. 60/642,336, filed on Jan. 7, 2005, provisional application No. 60/642,356, filed on Jan. 7, 2005.

(51) Int. Cl.
*B01D 35/06* (2006.01)
(52) U.S. Cl. .................. 210/138; 210/222; 210/695; 436/20; 436/56; 436/526; 435/173.1; 422/186.01; 366/273
(58) Field of Classification Search .............. 210/138, 210/222, 695; 436/20, 56, 526; 435/173.1; 422/186.01; 366/273
See application file for complete search history.

(56) References Cited

U.S. PATENT DOCUMENTS

| 6,033,574 | A | * | 3/2000 | Siddiqi ................ 210/695 |
|---|---|---|---|---|
| 6,326,144 | B1 | | 12/2001 | Bawendi et al. |
| 6,468,808 | B1 | | 10/2002 | Nie et al. |
| 6,623,982 | B1 | | 9/2003 | Liberti et al. |
| 6,645,731 | B2 | | 11/2003 | Terstappen |
| 2002/0098529 | A1 | | 7/2002 | Tan et al. |
| 2004/0067503 | A1 | | 4/2004 | Tan et al. |
| 2004/0137430 | A1 | | 7/2004 | Anderson et al. |
| 2004/0157271 | A1 | | 8/2004 | Kirakossian et al. |
| 2008/0135490 | A1 | | 6/2008 | Li et al. |

OTHER PUBLICATIONS

Amagliani, G., et al., "Direct detection of *Listeria monocytogenes* from milk by magnetic based DNA isolation and PCR." Food Microbiol. 21(5):597-603 (2004).

(Continued)

*Primary Examiner*—David A Reifsnyder
(74) *Attorney, Agent, or Firm*—Michael Best & Friedrich LLP

(57) ABSTRACT

Methods are disclosed for the capture, detection, separation, isolation and quantification of contaminants in a starting material. Also disclosed are competitive assay methods for the detection and quantification of contaminants in a starting material. Kits for use with the method are disclosed as well. A system for capturing, separating and/or concentrating contaminants from a material is also presented. The system captures, separates and/or concentrates contaminants such as bacteria, viruses, other microorganisms, and/or larger items, such as insects, from a variety of materials, such as food, and environmental and clinical materials. In general, the system uses a rotating magnetic field to mix the material with magnetic particles to capture the target contaminants, and a fixed magnetic field to separate and concentrate the captured target contaminants.

17 Claims, 17 Drawing Sheets

OTHER PUBLICATIONS

Ball, H. J., et al. "The detection of verocytotoxins in bacterial cultures from human diarrheal samples with monoclonal antibody-based ELISAS." J. Med. Microbiol. 44(4):273-276 (Apr. 1996).
Bennett, A. R., et al., "The isolation and detection of *Escherichia coli* O157 by use of immunomagnetic separation and immunoassay procedures." Lett. Appl. Microbiol. 22(3):237-243 (Mar. 1996).
Bruchez Jr., M, et al., "Semiconductor nanocrystals as fluorescent biological labels." Science 281(5385):2013-2016 (Sep. 25, 1998).
Captivate™ ferrofluid conjugates and related products, MP 21473. Rev: Dec. 3, 2001. Molecular Probes, Eugene, OR, USA.
Centers for Disease Control and Prevention (CDC). "Disease Information- *E. coli* O157:H7." website (www.cdc.gov) (2004).
Chan, W. C., et al., "Quantum dot bioconjugates for ultrasensitive nonisotopic detection." Science 281(5385):2016-2018 (Sep. 25, 1998).
Chapman, P.A. et al., "Use of commercial enzyme immunoassays and immunomagnetic separation systems for detecting *Escherichia coli* O157 in bovine fecal samples." Applied and Environmental Microbiology 63(7):2549-2553 (Jul. 1997).
Che, Y. H., et al., "Rapid detection of *Salmonella typhimurium* in chicken carcass wash water using an immunoelectrochemical method." J. Food Protect. 63(8):1043-1048 (Aug. 2000).
Che, Y. H., et al., "Rapid detection of *Salmonella typhimurium* using an immunoelectrochemical method coupled with immunomagnetic separation." J. Rapid Methods Automat. Microbiol. 7:47-59 (1999).
Cloak, O. M., et al., "Development of a surface adhesion immunofluorescent technique for rapid detection of *Salmonella* spp. from meat and poultry." J. Appl. Microbiol. 86(4):583-590 (Apr. 1999).
Deisingh, A. K., et al., "Strategies for the detection of *Escherichia coli* O157:H7 in foods." *J. Appl. Microbiol.* 96(3):419-429 (2004).
Dubertret, B., et al., "In vivo imaging of quantum dots enscapsulated in phospholipid micelles." Science 298(5599):1759-1762 (Nov. 29, 2002).
Fratamico, P. M., et al., "Rapid isolation of *Escherichia coli* O157:H7 from enrichment cultures of foods using an immunomagnetic separation method." Food Microbiol. 9(2):105-111 (1992).
Fritzsche, W., et al., "Metal nanoparticles as labels for heterogeneous, chip-based DNA detection." Nanotechnology 14:R63-R73 (2003).
Gehring, A. G., et al., "Enzyme-linked immunomagnetic electrochemical detection of *Salmonella typhimurium*." J. Immunol. Methods 195(1-2):15-25 (Sep. 9, 1996).
Gehring A.G. et al., "Use of a light-addressable potentiometric sensor for the detection of *Escherichia coli* O157:H7." Anal Biochem 258(2):293-298 (May 1, 1998).
Gu, H., et al., "Biofunctional magnetic nanoparticles for pathogen detection." 226th ACS National Meeting, NY. ACS, Washington DC, USA (2003).
Gu, H., et al. "Using biofunctional magnetic nanoparticles to capture Gram-negative bacteria at an ultra-low concentration." Chemical Communications (Cambridge, United Kingdom) 15:1966-1967 (Aug. 7, 2003).
Hage, D. S. "Immunoassays." Anal. Chem. 71:294R-304R (1991).
Jaiswal, J. K., et al., "Long-term multiple color imaging of live cells using quantum dot bioconjugates." Nat. Biotechnol. 21(1):47-51 (Jan. 2003).
Karch, H., "Isolation of Enterohemorrhagic *Escherichia coli* O157 Strains from Patients with Hemolytic-Uremic Syndrome by Using Immunomagnetic Separation, DNA-Based Methods, and Direct Culture" Journal of Clinical Microbiology 34(3):516-519 (Mar. 1996).
Kemshead, J. T., et al., "A model system for the enrichment of tumor cells from peripheral blood and bone marrow using immuno-magnetic ferrofluids" p. 593-600. Advances in bone marrow purging and processing. Fourth International Symposium on Bone Marrow Purging and Processing. Orlando, Florida, USA (1993).
Kemshead, J.T. et al., "Immunomagnetic Colloids for the Enrichment of Tumor Cells from Peripheral Blood and Bone Marrow: A Model System" Journal of Hematotherapy 3(1):51-57 (Spring 1994).
Larson, D.R., et al., "Water-soluble quantum dots for multiphoton fluorescence imaging in vivo." Science 300(5624):1434-1436 (May 30, 2003).
Lekowska-Kochaniak, A., D. et al., "Detection of *Escherichia coli* O157:H7 in raw meat by immunomagnetic separation and multiplex PCR." Acta Microbiol. Pol. 51(4):327-337 (2002).
Li, J., et al., "Piezoelectric immunosensor based on the magnetic nanoparticles with simple immobilization procedures." Anal. Chemica Acta 481:191-198 (2003).
Liberti, P. A., et al, "Bioreceptor ferrofluids: novel characteristics and their utility in medical applications.", p. 777-790. In E. Pelizzetti (ed.), Fine Particles Science and Technology. Kluwer Academic Publishers, Netherlands (1996).
Liu, R. H., et al., "Accoustic microstreaming for biological sample mixing enhancement." p. 545-550. 2nd Annual International IEEE-EMBS Special Topic Conference on Microtechnologies in Medicine & Biology. Madison, WI, USA (May 2-4, 2002), Poster 183.
Liu, Y., et al., "Rapid detection of *E. coli* O157:H7 inoculated in ground beef, chicken carcass, and lettuce samples with an immunomagnetic chemiluminescence fiber-optic biosensor." J. Food Prot. 66(3):512-517 (Mar. 2003).
Mansfield, L.P., et al., "The detection of *Salmonella* using a combined immunomagnetic separation and ELISA end-detection procedure." Lett. Appl. Microbiol. 31(4):279-283 (May 30, 2003).
Oleschuk, R. D., et al., "Trapping of bead-based reagents within microfluidic systems: On-chip solid-phase extraction and electrochromatography." Anal. Chem. 72(3):585-590 (Feb. 1, 2000).
Olsvik, O., et al., "Magnetic separation techniques in Diagnostic Microbiology." Clin. Microbiol. Rev. 7(1):43-54 (Jan. 1994).
Owen, C. S., "Magnetic sorting of leukocytes." Cell Biophy. 8(4):287-296 (Aug. 1986).
Parmar, N., et al., "The detection of *Salmonella enteritidis* and *Salmonella typhimurium* using immunomagnetic separation and conductance microbiology." Lett. Appl. Microbiol. 15:175-178 (1992).
Peng, T., et al., "Amperometric detection of *Eschericia coli* heat-labile enterotoxin by redox diacetylenic vesicles on a sol-gel thin-film electrode." Anal. Chem. 72(7):1611-1617 (Apr. 1, 2000).
Peng, Z.G. et al. "Conformational Change of Adsorbed and Desorbed Bovine Serum Albumin on Nano-sized Magnetic Particles" Colloids and Surfaces B: Biointerfaces 33:15-21 (2004).
Pérez, F.G. et al. "Immunomagnetic Separation with Mediated Flow Injection Analysis Amperometric Detection of Viable *Escherichia coli* O157" Anal. Chem. 70(11):2380-2386 (Jun. 1, 1998).
Pyle, B. H., et al., "Sensitive detection of *E. coli* O157 in food and water by immunomagnetic separation and solid-phase laser cytometry." Appl. Environ. Microbiol. 65(5):1966-1972 (May 1999).
Rosenthal, S. J., et al., "Targeting cell surface receptors with ligand-conjugated nanocrystals." J. Am. Chem. Soc. 124(17):4586-4594 (May 1, 2002).
Ruan, C., et al. "A Biensyme Electrochemical Biosensor Coupled with Immunomagnetic Separation for Rapid Detection of *Escherichia coli* O157:H7 in Food Samples" Transactions of the ASAE 45(1):249-255 (2002).
Sathaye, A., et al., "An acoustic vortex generation for microfluidic particle entrapment." p. 641-644, vol. 1. IEEE Ultrasonics Symposium. Atlanta, Georgia, USA (2001).
Seo K. H., et al., "Immunomagnetic separation and flow cytometry for raipd detection of *Escherichia coli* O157:H7." Journal of Food Protection. 61(7):812-816 (Jul. 1998).
Seong, G. H., et al., "Efficient mixing and reactions within microfluidic channels using microbead-supported catalysts." J. Am. Chem. Soc. 124(45):13360-13361 (Nov. 13, 2002).
Shaw, S. T., et al., "Performance of the Dynabeads anti-*Samonella* system in the detection of *Salmonella* species in foods, animal feeds, and environmental samples." J. Food Protect. 61(11):1507-1510 (Nov. 1998).
Soukka, T., et al., "Utilization of kinetically enhanced monovalent binding affinity by immunoassays based on multivalent nanoparticles-antibody bioconjugation." Anal. Chem. 73(14):2254-2260 (Jul. 15, 2001).
Stoimenov, P. K., et al., "Metal oxide nanoparticles as bactericidal agents." Langmuir 18:6679-6686 (2002).
Su, L. et al. "Quantum dots as fluorescent probes for detection of *Escherichia coli* O157:H7." Presented orally at *The 2004 Annual Meeting of the Institute of Biological Engineering (IBE)*, Jan. 9-11, 2004, Fayetteville, Arkansas.

Su, X., et al., "Quantum dot biolabeling coupled with immunomagnetic separation for detection of *Escherichia coli* O157:H7" Analytical Chemistry 76(16):4806-4810 (Aug. 15, 2004).

Sun, W., et al., "Comparison of ATP and in vivo Bioluminescence for Assessing the Efficiency of Immunomagnetic Sorbents for Live *Escherichia coli* O157:H7 Cells" Journal of Applied Microbiology 92(6):1021-1027 (2002).

Tan, W., et al., "Bionanotechnology based on silica nanoparticles." Med. Res. Rev. 24(5):621-638 (Sep. 2004).

Tibbe, A. G. J., et al., "Cell analysis system based on compact disk technology." Cytometry 47(3):173-182 (Mar. 1, 2002).

Tibbe, A. G. J., et al., "Magnetic field design for selecting and aligning immunomagnetic labeled cells." Cytometry 47(3):163-172 (Mar. 1, 2002).

Tibbe, A. G. J., et al., "Optical tracking and detection of immunomagnetically selected and aligned cells." Nat. Biotechnol. 17(12):1210-1213 (Dec. 1999).

Varshney M., et al., "Magnetic Nanoparticle-Antibody Conjugates for the Separation of *Escherichia coli* o157:H7 in Ground Beef" J Food Protection 68(9):1804-1811 (Sep. 2005).

Varshney, M., et al., "Magnetic Immuno-nanoparticles for highly efficient separation of *Escherichia coli* O157:H7 from food samples." A poster presented at the Arkansas Section of ASAE 2004 Annual Meeting, Little Rock, AR (Oct. 1, 2004).

Varshney, M., et al., "A chemiluminescence biosensor coupled with immunomagnetic separation for rapid detection of *Salmonella typhimurium*." J. Rapid Meth. Automat. Micobiol. 11:111-131 (2003).

Varshney, M., et al., "Magnetic immuno-nanoparticles for hightly efficient separation of *Escherichia coli* O157:H7 from food samples." A poster presented at the Food Safety Consortium 2004 Annual Meeting, Oct. 3-5, Ames, IA. Abstract of the poster in: CD of Food Safety Consortium 2004 Annual Meeting—Agenda, Presentations, and Progress Reports.

Wang, H., et al., "PCR based fluorescent method for rapid detection of *Salmonella typhimurium* in poultry samples." J. Rapid Meths. Auto. Microbiol. 10:83-92 (2002).

Watson, A., et al., "Lighting up cells with quantum dots" Biotech. 34(2):296-303 (Feb. 2003).

Wu, X., et al., "Immunofluorescent labeling of cancer marker Her2 and other cellular target with semiconductor quantum dots." Nat. Biotechnol. 21(1):41-46 (Jan. 2003).

Yang, L., et al., "Rapid detection of *Salmonella typhimurium* in food samples using a bienzyme electrochemical biosensor with flow injection." J. Rapid Methods Automat. Microbiol. 9:229-240 (2001).

Yang, L., et al., "Interdigitated array microelectrode-based electrochemical impedance immunosensor for detection of *Escherichia coli* O157:H7." Anal. Chem. 76(4):1107-1113 (Feb. 15, 2004).

Ye, J., "A Chemiluminescence Fiber-optic Biosensor Coupled with Immunomagnetic Separation for Rapid Detection of *E. Coli* O157:H7" Transactions of the ASAE 45(2):473-478 (2002).

Yu, H., et al., "Immunomagnetic-electrochemiluminescent Detection of *Escherichia coli* O157 and *Salmonella typhimurium* in Foods and Environmental Water Samples" Applied and Environmental Microbiology 62(2):587-592 (Feb. 1996).

Yu, L.S.L., et al., "Immunomagnetic Separation Methods for the Isolation of *Campylobacter jejuni* from Ground Poultry Meats" Journal of Immunological Methods 256(1-2):11-18 (Oct. 1, 2001).

Zhao, X., et al., "A Rapid Bioassay For Single Bacterial Cell Quantitation Using Bioconjugated Nanoparticles" PNAS 101(42):15027-15032 (Oct. 19, 2004).

Zhu, L., et al., "Quantum dots as a novel immunofluoresecent detection system for *Cryptosporidium parvum* and *Giardia lamblia*." Appl. Environ. Microbiol. 7(1)0:597-598 (Jan. 2004).

United States Patent Office Action for U.S. Appl. No. 11/328,020 dated Nov. 13, 2008 (11 pages).

\* cited by examiner (a)

(b)

SEPARATION SYSTEM AND EFFICIENT CAPTURE OF CONTAMINANTS USING MAGNETIC NANOPARTICLES

CROSS-REFERENCE TO RELATED APPLICATIONS

This application claims the benefit of U.S. provisional application 60/642,336, and 60/642,356, both filed on Jan. 7, 2005. These provisional applications are incorporated herein by reference in their entireties.

STATEMENT REGARDING FEDERALLY SPONSORED RESEARCH

The invention was made with United States government support under Grant Number USDA/CSREES 99-34211-7563 awarded by the United States Department of Agriculture. The United States government has certain rights in this invention.

INTRODUCTION

The ability to detect the presence of small amounts of contaminants, such as bacteria, in a complex background is of vital importance to biotechnology, medical diagnosis and the fight against bioterrorism. Detection and identification of contaminants in the food or water supply is necessary to protect health and safety as many microorganisms become resistant to antibiotics and the threat of bioterrorism grows. Also, rapid detection of small amounts of contaminants will result in faster clinical diagnosis of disease, and may result in better prognosis. Detection of contaminants is difficult when only a small amount must be detected in a large sample volume or within a complex sample such as a food product or soil. There exists a need in the art for additional methods for capturing, detecting, separating and quantifying contaminants that are sensitive, specific and rapid.

Beads, particularly microbeads, and more particularly magnetic microbeads, have been widely used to develop methods for separating or isolating a variety of biomolecules and other contaminants from complex starting materials. In particular, immunomagnetic microbeads (antibody-coated) provide a specific, technically simple, rapid and efficient method of isolating a target material, such as bacteria, from starting materials. The bacteria captured by antibody-coated microbeads may be detected by conventional plating, which is reliable, but generally time-consuming, requiring 18 or more hours. Several methods for rapid detection have been reported and are based on either use of enzyme or fluorescently labeled secondary antibodies followed by optical or electrochemical analysis. Additionally, biosensors have been developed to automate detection of contaminants. Some of these biosensors use antibody-conjugated microbeads to bind and capture the contaminants.

Nanoparticles range in size from 1 to 300 nm in diameter and exhibit properties of a fluid rather than a particle. Nanoparticles may be magnetic or may serve as a calorimetric label as described by Fritzsche and Taton, Nanotechnol. 14:R63-R73 (2003); Tan et al., Med. Res. Rev. 24:621-638 (2004); Zhao et al., PNAS 101:15027-15032 (2004); U.S. Pat. No. 6,623,982; and U.S. Pat. No. 6,645,731 all of which are incorporated herein by reference in their entireties. Magnetic nanoparticles do not interfere with chemiluminescence, fluorescence, PCR analysis or immunoassays.

SUMMARY

Methods are provided for capturing, detecting, separating, isolating and quantifying contaminants in a variety of starting materials including, but not limited to food products, clinical samples and environmental samples. More specifically, methods are provided for the sensitive, specific and rapid detection, separation and quantification of contaminants in a untreated starting material using magnetic nanoparticles. In one aspect, methods of separating a contaminant from an untreated starting material are described. The method includes immunolabeling a contaminant in the untreated starting material followed by nanomagnetically separating the contaminant from the untreated starting material.

Another method comprises contacting the untreated starting material with an affinity moiety capable of binding the contaminant to form a target comprising the affinity moiety bound to the contaminant. The target is then contacted with a magnetic nanoparticle capable of binding the affinity moiety to form a magnetic target which is then separated from the untreated starting material.

In another aspect, kits for separating a contaminant from a untreated starting material are provided. The kits include a magnetic nanoparticle capable of binding an affinity moiety and an affinity moiety capable of binding the contaminant. The kits may optionally include at least solution containing a known amount of the contaminant to aid in quantifying the amount of the contaminant present in the starting material.

In yet another aspect, methods of separating a contaminant from a starting material are described. The method consists of homogenizing the starting material. The homogenized starting material is contacted with an affinity moiety capable of binding the contaminant to form a target. The target is then contacted with a magnetic nanoparticle capable of binding the affinity moiety to form a magnetic target that is separated from the homogenized starting material.

In a further aspect, competitive methods of detecting a contaminant in a starting material are described. The method includes contacting the starting material containing the contaminant and a control material not containing the contaminant with a marker coupled to an affinity moiety. The affinity moiety is capable of binding the contaminant, and the marker has a characteristic emission spectrum. The starting material and the control material are also contacted with a competitor complex comprising a magnetic nanoparticle coupled to the contaminant. The competitor complex is separated from each of the starting material and the control material. The characteristic emission spectrum of the marker associated with the competitor complex from each of the starting material and the control material is detected. A decrease in the intensity of the characteristic emission spectrum of the competitor complex from the starting material as compared to the intensity of the characteristic emission spectrum of the competitor complex from the control material is indicative of the presence of the contaminant in the starting material.

A system for capturing, separating and/or concentrating contaminants from a material is also presented. The system captures, separates and/or concentrates contaminants such as bacteria, viruses, other microorganisms, and/or larger items, such as insects, from a variety of materials, such as food, and environmental and clinical materials. The system has a highly efficient capture rate of about 90%, a relatively short operation time of about less than 20 minutes, and may produce a highly concentrated sample. In general, the system uses a rotating magnetic field to mix the material with magnetic particles to capture the target contaminants, and a fixed magnetic field to separate and concentrate the captured target contaminants.

The system may include a housing that supports a chamber into which materials and magnetic particles may be fed. In the chamber, the materials are mixed with magnetic particles to separate, capture and/or concentrate a target contaminant. The magnetic nanoparticles are coated with specific antibodies for capturing the target contaminant 110. The system also includes a controller and a magnetic field subsystem. The controller controls the magnetic field subsystem to produce the rotating and fixed magnetic fields use to separate out contaminants. The rotating magnetic fields push the magnetic particles in predetermined patterns by layers of rotating magnetic fields to bind the contaminant and the antibody. Then, the fixed magnetic attracts and holds the magnetic particles (and the contaminant) so that the remainder of the material may be washed away from the chamber. The collected contaminants may be diluted with a small volume of buffered solution and placed in a container.

BRIEF DESCRIPTION OF THE DRAWINGS

The methods and systems may be better understood with reference to the following drawings and description. The components in the figures are not necessarily to scale, emphasis instead being placed upon illustrating the principles. Moreover, in the figures, like referenced numerals designate corresponding parts throughout the different views.

Figure is an isometric drawing of an separation system.

DETAILED DESCRIPTION

Figure 1:
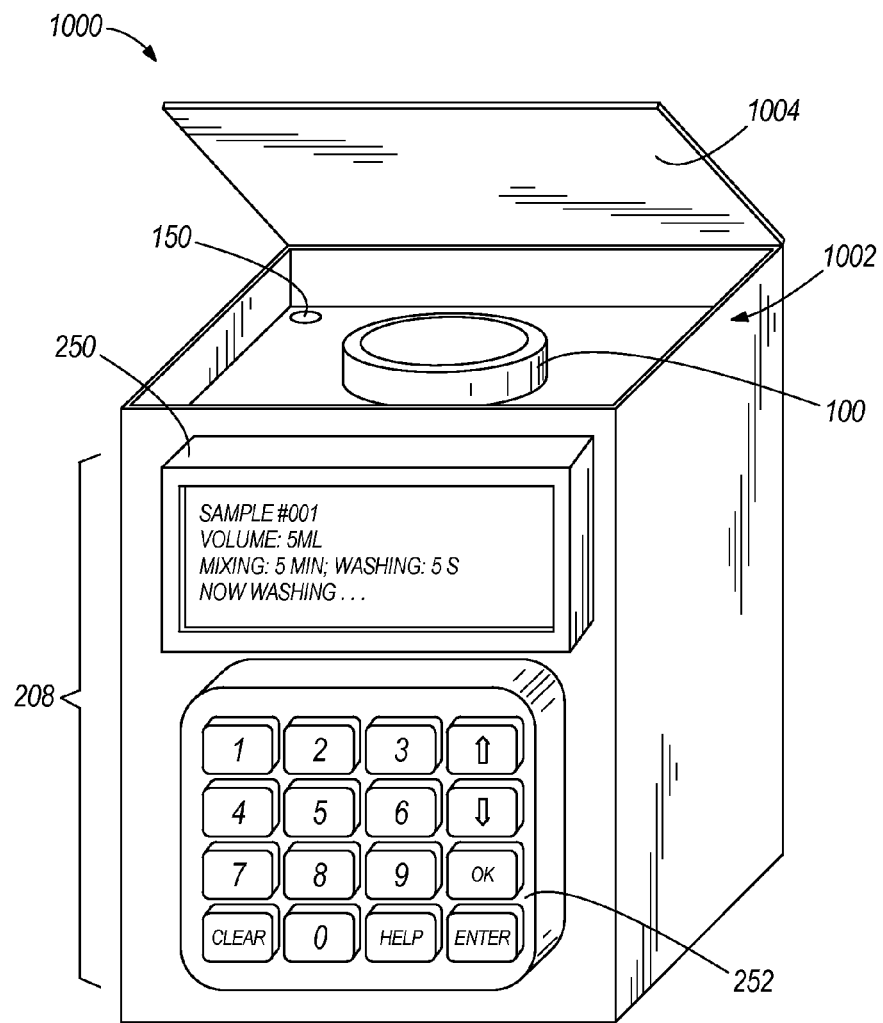

In the figures, the same reference symbols designate the same parts with the same significance unless otherwise indicated.

The development of rapid, sensitive and specific methods for capture, detection, separation, isolation and quantification of contaminants is a challenging and important task. Such methods are necessary to ensure food safety, environmental safety and security and may aid in early diagnosis of disease, resulting in better prognosis. Briefly, methods are provided for capturing, detecting, separating, isolating, and quantifying the amount of a contaminant in a minimally treated or untreated test sample or starting material by labeling the contaminant with an affinity moiety, suitably an antibody. The affinity moiety is capable of binding to the contaminant and is either bound to or is capable of binding to a magnetic nanoparticle. A magnetic target, comprised of the contaminant-affinity moiety-magnetic particle complex, is formed and may be separated from the starting material using magnetic separation techniques.

The methods described herein may be used to detect the presence of contaminants in a wide variety of starting materials with various levels of complexity in terms of antigenic diversity, density and volume. In addition to the starting materials used in the examples below, it is reasonable to expect that contaminants may be detected in a wide variety of food products, environmental and clinical samples and may include liquid, solid or materials containing a mixture of liquids and solids. The starting materials may include vegetables, fruits, ground meats, beef, poultry, sea food, dairy, water, air, soil, blood, urine, feces, swabs from the surface of the skin or organs, or tissue samples. Food samples may be raw or ready-to-eat. For example, a poultry product may include a chicken carcass, wash water from a chicken carcass, a deboned chicken, ground poultry meats or poultry patties. The methods are also suitable for food or environmental inspection or clinical diagnosis. For example, the methods may be used to monitor food during processing, storage, distribution or even once in the market. An untreated test sample or starting material refers to a material that is not filtered or centrifuged prior use in the method. A solid or semi-solid starting material may be subject to homogenization prior to use in the methods. The slurry resulting from blending or homogenization remains untreated.

As described in the Examples below, many types of contaminants may be captured detected, separated or quantified using the methods described herein. In the Examples, *Escherichia coli* O157:H7 and atrazine were detected. In addition to these contaminants, it is reasonable to expect that one of skill in the art may use the methods with a wide variety of potential contaminants including, but not limited to, bacteria such as *Listeria monocytogenes, Campylobacter jejuni, Pseudomonas mirabilis, Salmonella* species and *Enterococcus* species; eukaryotic cells; polypeptides, including prions, toxins and blood or urine proteins; viruses; or other chemical contaminants such as pesticides or herbicides. Significantly, both live and dead cells may be detected by the methods described herein. Starting materials, however, may be pretreated to kill any live contaminants that may pose a health risk to a technician performing the method described herein.

Nanoparticles have previously been described. See Varshney et al., J Food Protection 68:1804-1811 (2005); Fritzsche and Taton, Nanotechnol. 14:R63-R73 (2003); Tan et al., Med. Res. Rev. 24:621-638 (2004); Zhao et al., PNAS 101:15027-15032 (2004); U.S. Pat. No. 6,623,982; and U.S. Pat. No. 6,645,731 all of which are incorporated herein by reference in their entireties. Nanoparticles range in size from 1-300 nm in diameter, suitably from 50-150 nm in diameter. Nanoparticles may have a magnetic core that may include various metals and, like microbeads, the magnetic core may be paramagnetic or superparamagnetic. Nanoparticles may also include a pigmented core or a dye. Nanoparticles suitable for use in the methods described herein include those commercially available from Molecular Probes, Inc. (Eugene, Oreg.).

Once the beads are contacted with the starting material and the magnetic target is formed, the magnetic target may be separated from the starting material in a variety of ways. Beads may be separated by filtration, centrifugation or by generation of a magnetic field. Magnetic separation devices suitable for use in the methods include the Magnetic Particle Concentrator (MPC) from Dynal, Inc. (Lake Success, N.Y.) and the separation system described below.

The nanoparticles may be directly or indirectly coupled to affinity moieties having affinity for the contaminant. Nanoparticles are commercially available already prepared for coupling to affinity moieties by a variety of chemical reactions, but may also be prepared by the end-user. Nanoparticles may be coupled to affinity moieties by a variety of methods including, but not limited to, pre-conjugation to streptavidin, avidin, Protein G or Protein A; use of commercially available kits for binding nanoparticles directly to antibodies via a covalent linkage; nanoparticles with functional carboxy or amino groups exposed on their surface for use in coupling a variety of polypeptides; or nanoparticles linked to a polypeptide (a linker) capable of binding either the Fc region of an antibody, such as an Fc receptor or anti-Fc antibody, or a non-Fc region of the antibody. Polypeptides may be biotinylated by methods well known to those of skill in the art and the biotin may form a bridging complex linking a nanoparticle to an affinity moiety by binding to streptavidin or avidin. It is reasonable to expect that one of skill in the art may utilize a variety of different chemistries to couple the affinity moiety to the nanoparticles either directly or indirectly. These same coupling methods may be used to couple a contaminant to a nanoparticle for use in a competitive assay, such as that described in Example 9.

The magnetic nanoparticles are able to bind to the contaminant by virtue of their coupling to an affinity moiety. Affinity moieties are suitably polypeptides that have affinity for the contaminant and will bind to the contaminant when brought into proximity with it. Affinity moieties include antibodies specific for the contaminant, ligands capable of binding a receptor on the contaminant, and receptors that bind to the contaminant. In addition to those affinity moieties exemplified below as useful in the methods described herein, it is reasonably expected that other antibodies, known to those of skill in the art, with affinity for various contaminants will be suitable. Suitable antibodies may be identified using an antibody source guide, for example Linscott's Directory of Immunological and Biological Reagents or the MSRS Catalog of Primary Antibodies. Methods for generating monoclonal and polyclonal antibodies are known to those of skill in the art.

The steps of the method may be completed in several different orders. For example, the affinity moiety may be coupled to the magnetic nanoparticle prior to contact with the starting material, or it may be added after the contaminant-affinity moiety complex is formed. Alternatively, the affinity moiety and the magnetic nanoparticle may be added to the starting material simultaneously. The magnetic target may be separated from the remainder of the starting material using any magnetic separator, including, but not limited to the magnetic separation device described herein. The magnetic target may also be used in biosensors, including but not limited to, impedance biosensors, quartz crystal microbalance biosensors and viscoelastic biosensors as described in U.S. Provisional Patent Application No. 60/642,335, entitled "VISCOELASTIC BIOSENSOR BASED ON IMMUNOMAGNETIC BEADS FOR DETECTION OF BACTERIAL PATHOGENS", filed Jan. 7, 2005 and its corresponding U.S. Utility Application, filed Jan. 9, 2006.

The magnetic target may also be labeled using fluorescent markers, such as fluorophores or quantum dots. Quantum dots are fluorescent semiconductor nanocrystals and represent a relatively new class of fluorescent markers. Quantum dots may be modified and used to label biologic samples as previously described by Chan and Nie, Science 281:2016-2018 (1998); Bruchez et al., Science 281:2013-2016 (1998); U.S. Pat. No. 6,326,144; and U.S. Pat. No. 6,468,808 all of which are incorporated herein by reference in their entireties. For example, proteins may be covalently attached to quantum dots and interactions of the protein with other molecules monitored by fluorescent microscopy. Quantum dots have several advantages over conventional fluorescent dyes. They have narrow emission spectra, broad absorption spectra, are photostable and the emission color is tunable by changing the size and material composition of the quantum dot core.

The magnetic target resulting from the separation step of the present method may subsequently be utilized in various microbiologic, immunologic or nucleic acid based assays. For example, the contaminant may be isolated from the magnetic target and either the contaminant or the magnetic target may be subjected to assays including, but not limited to antibiotic resistance testing, ELISA assays, colony forming unit assays, histological staining, and polymerase chain reaction assays.

In addition, methods for performing a competitive detection assay for detecting the presence and quantifying the amount of a contaminant in a starting material are described. The method involves contacting the starting material containing a contaminant, and a control material that does not contain the contaminant with two compositions. The first composition comprises a marker, such as a fluorescent marker, coupled to an affinity moiety. The second composition comprises a magnetic nanoparticle coupled to the contaminant to form a competitor complex. The competitor complex will compete with the contaminant in the starting material to bind the affinity moiety coupled to the marker. After a period of mixing, the competitor complex with any associated marker is separated from the starting material and the control material. The characteristic emission spectrum of the marker associated with the competitor complex in both the starting material and the control material is detected. A decrease in the intensity of the characteristic emission spectrum associated with the competitor complex from the starting material as compared to the intensity of the characteristic emission spectrum associated with the competitor complex from the control material is indicative of the presence of the contaminant in the starting material. This method may also provide quantitative information if the characteristic emission spectrum of the competitor complex from the starting material is compared to the characteristic emission spectrum of the competitor complex from control samples containing known amounts of the contaminant. The amount of decrease in the intensity of the characteristic emission spectrum of the competitor complex from the starting material relative to the intensity of the emission spectrum of the competitor complex from the control is indicative of the quantity of the contaminant in the starting material.

As discussed above, magnetic separation devices, such as immunoseparation devices may be used to separate a magnetic target from a starting material. An example of a system for capturing, separating and/or concentrating contaminants from a material is shown in FIG. 1. The system 1000 may capture, separate and/or concentrate contaminants such as bacteria, viruses, other microorganisms, and/or larger items, such as insects, from a variety of materials, such as food, and environmental and clinical materials. The system 1000 has a highly efficient capture rate of about 90%, a relatively short operation time of about less than 20 minutes, and may produce a highly concentrated sample (10-1,000 times). The system 1000 may be automatic and/or portable.

In general the system 1000 uses a rotating magnetic field to mix the material with magnetic particles to capture the target contaminants, and a fixed magnetic field to separate and concentrate the captured target contaminants. For example, the system 1000 may mix a material with antibody modified magnetic nanoparticles to specifically capture, separate and concentrate target microorganisms. As shown in FIG. 1, the system 1000 may include a chamber 100 and an inlet 150. Materials may be fed into the chamber 100 through the inlet 150, perhaps with a syringe. In the chamber 100, the materials are mixed with magnetic particles to separate, capture and/or concentrate a target contaminant. The system 1000 may also include a housing 1002 that supports some or all of the elements of the system 1000. The housing 1002 may also include a covering. In this example, the housing 1002 supports a user interface 208 that enables communication between a user or other system and the separation system 1000. The user interface 208 includes an LCD screen that displays the contents of the chamber 1002 and the status of a separation operation. In addition, the user interface 108 includes a keyboard 252 by which a user may communicate commands and parameter values to the system 1000.

Figure 2A:
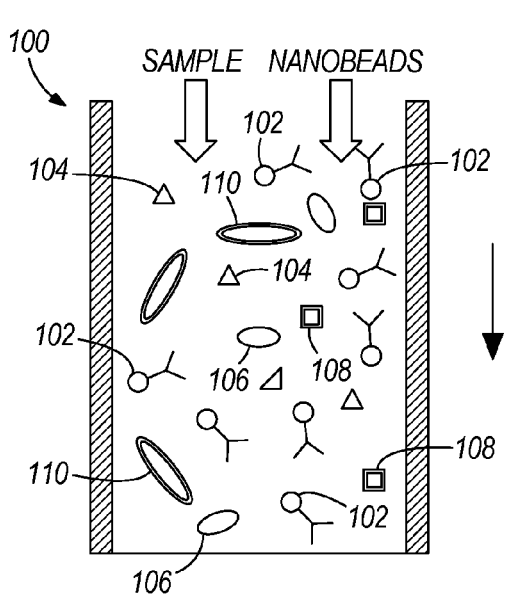
FIG. 2A is a diagram of a sample and nanobeads placed into a chamber of an separation system.
Figure 2B:
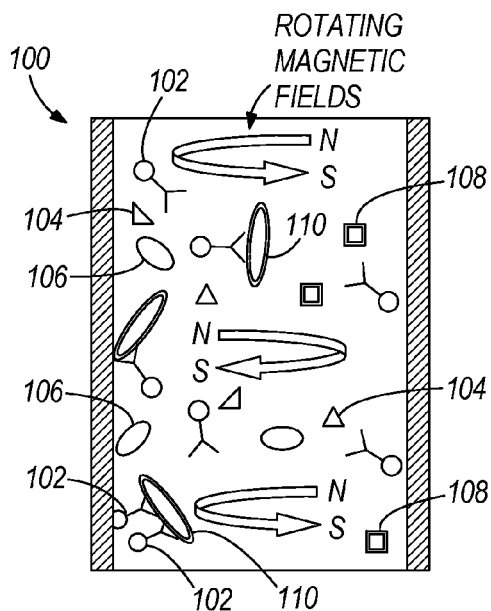
FIG. 2B is a diagram of a rotating magnetic field applied to the chamber of FIG. 2A.
Figure 2C:
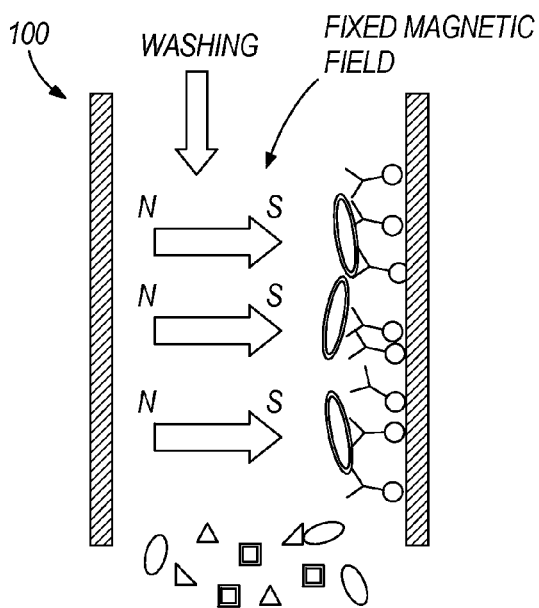
FIG. 2C is a diagram of a fixed magnetic field applied to the chamber of FIG. 2A.
Figure 2D:
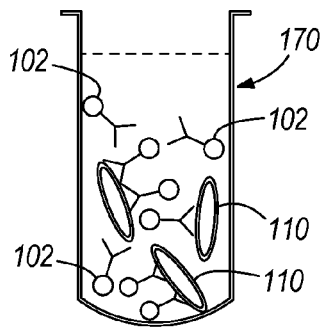
FIG. 2D is a diagram of a target contaminant in a container.

A example of the process by which the system 1000 captures, separates and concentrates contaminants from a material is shown in FIGS. 2A-2D. As shown in FIG. 2A, a material (or sample of the material) and magnetic nanoparticles 102 are inserted into the chamber 100. The material includes particles 102, 104, 106, 108, and a target bacteria 110. The magnetic nanoparticles 102 are coated with specific antibodies for capturing the target contaminant 110. In FIG. 2B, the system 1000 applies a rotating magnetic field within the chamber 100 to mix the material with magnetic nanoparticles 102. The magnetic nanoparticles 102 are pushed in predetermined patterns by layers of rotating magnetic fields for a time period, such as 15 minutes, to bind the antigens on target bacteria 110. Then, as shown in FIG. 2C, the system 1000 applies a constant magnetic field within the chamber 100, which attracts and holds the magnetic nanoparticles 102, including those with bacteria 110 and free nanoparticles. The remainder of the particles 102, 104, 106, 108 found in the material may be washed away from the chamber 100. Finally, the collected magnetic nanoparticles (with or without bacteria 110) may be diluted with a small volume of buffered solution and placed in a container. The concentrated bacteria 120 may be stored for further use in microbial plating, ELISA, PCR, biosensors and other applications.

Figure 3:
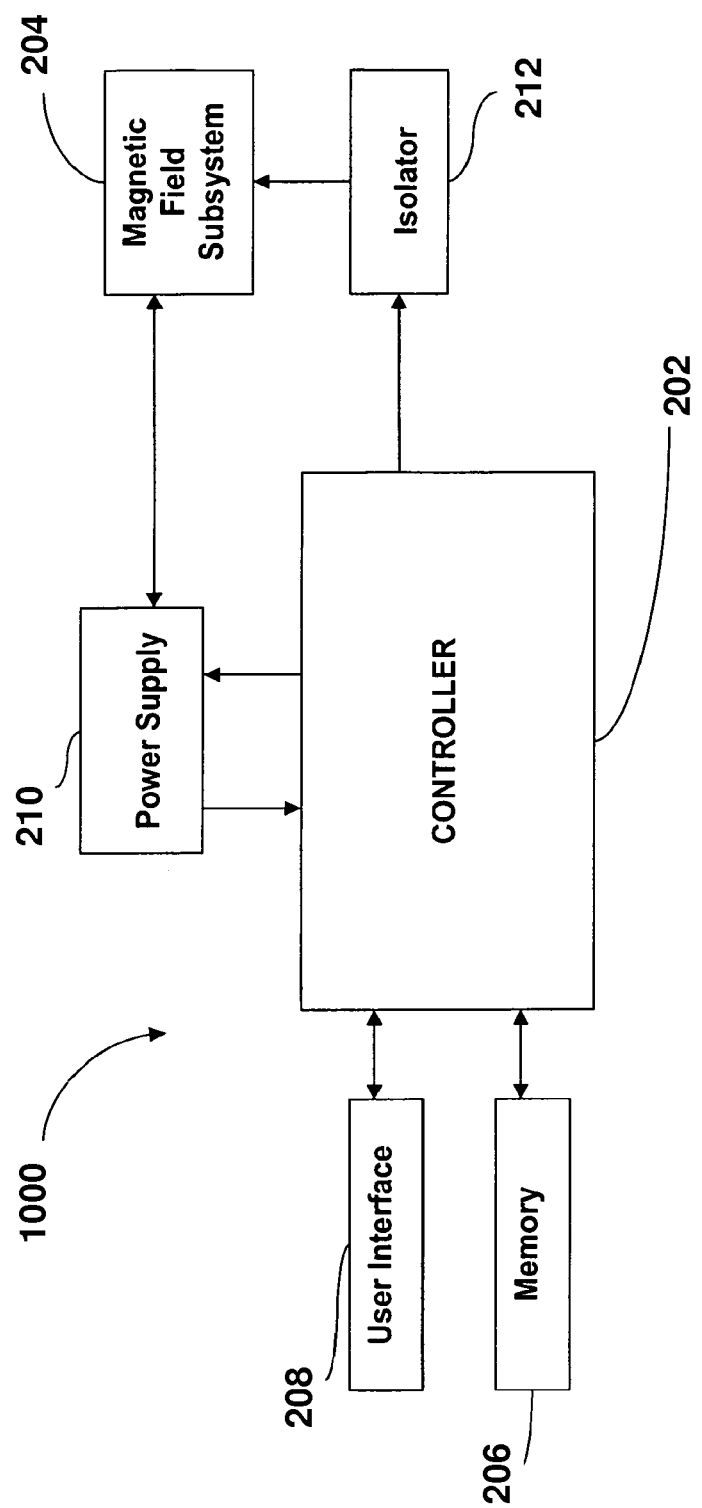
FIG. 3 is a functional block diagram of a separation system.

A block diagram of the functional components of the system 1000 is shown in FIG. 3. In general, the system 1000 includes a controller 202 and a magnetic field subsystem 204. The controller 202 controls the magnetic field subsystem 204 to produce the rotating and fixed magnetic fields use to separate out contaminants. The system 1000 may also include a memory 206, user interface 208, power supply 210, and an isolator 212.

Figure 4:
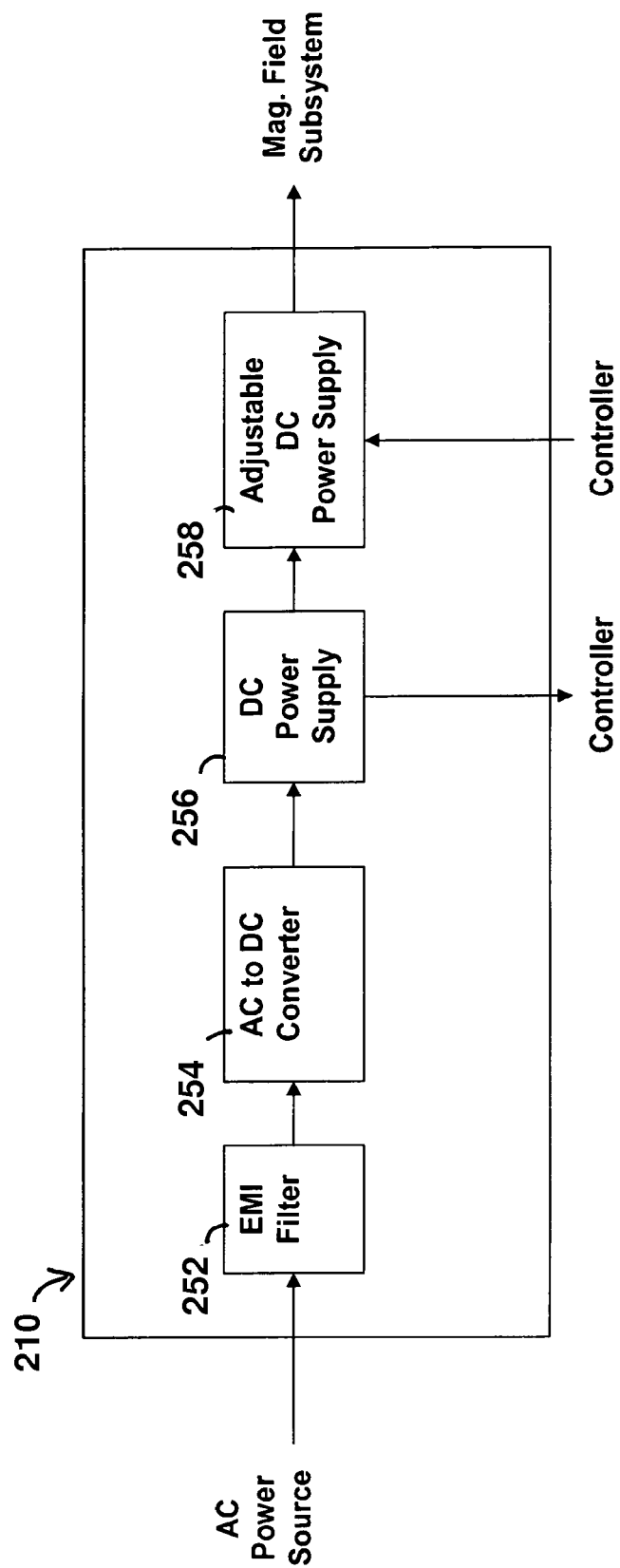
FIG. 4 is a block diagram of a power supply.

As shown in FIG. 4, the power supply 210 produces DC power (adjustable and fixed) from AC power received from an AC power source. The power supply 210 generally includes an AC to DC converter 254, a DC power supply 256, and an adjustable DC power supply 258. The DC power supply 256 produces the fixed voltages needed to drive many of the other components of the system, such as the controller 202. The adjustable DC power supply 258 is controlled by the controller 202 to produce the varying voltage needed to operate the magnetic field subsystem 204. In addition, the power supply 210 may include an EMI filter 252 to protect the components of the system 1000 from electromagnetic interference.

Figure 5:
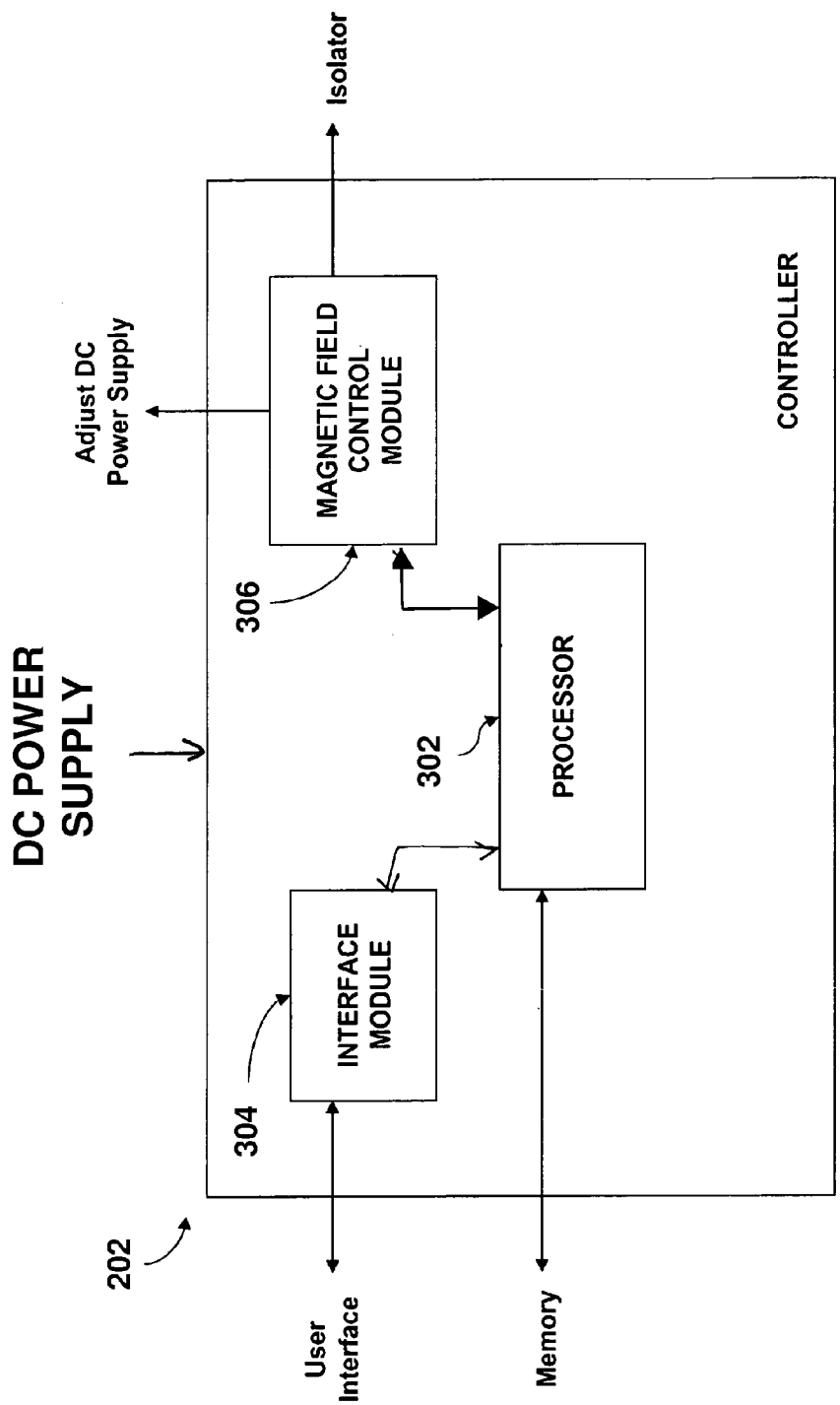
FIG. 5 is a block diagram of a controller.

The functional components of the controller 202 are shown in more detail in FIG. 5 with references made to elements in FIG. 3. The controller 202 may include a processor 302, interface module 304, magnetic field control module 306, and/or memory (not shown). The controller 202 may communicate with the user interface 208, memory 206, power supply 210, isolator 212, and magnetic field subsystem 204 using any type of electromagnetic communications via any electromagnetic channel or network. The processor 302 may include any type of device or devices used to process digital information. The interface module 304 facilitates communication between the processor 302 and the user interface 208. The magnetic field control module 306 controls the operation of the magnetic field subsystem 204 by controlling the adjustable DC power supply 258 (FIG. 4) and sending other control signals. The control module 306 may adjust parameters according to input received from the user interface via the interface module 304 and/or information stored in the memory 206. The parameters include: magnetic strength (coil working voltage), magnetic field direction (coil on/off sequence), and magnetic field speed (coil time interval) for each layer, mixing time (rotating magnetic field), and washing time (constant magnetic field). To prevent damage from noise produced by the magnetic field subsystem 204, the controller 202 may communicate with the magnetic field subsystem 204 via an isolator 212, such as an optical isolator.

Referring to FIG. 3, the user interface 208 generally serves as an interface with the controller 202, to which it may be directly or indirectly coupled. The user interface 208 may reside remotely or within the same assembly as the controller 202. The user interface 208 may include an input module and an output module. The output module may be any type of visual, manual, audio, electronic or electromagnetic device capable of communicating information from a processor or memory to a person or other processor or memory. Examples of output devices include, but are not limited to, monitors, speakers, liquid crystal displays (such as that shown in FIG. 1), networks, buses, and interfaces. The input device may be any type of visual, manual, mechanical, audio, electronic, or electromagnetic device capable of communicating information from a person, or memory to a processor or memory. Examples of input devices include keyboards (such as that shown in FIG. 1), microphones, voice recognition systems, trackballs, mice, networks, buses, and interfaces. Alternatively, the input and output devices may be included in a single device such as a touch screen, computer, processor, memory coupled with or a port for coupling the foregoing with the controller 202 via a network. The user interface 208 include one or more processors and one or more computer-readable memories (not shown).

Further, the immunoseparation system 1000 may include a memory 206 that is in communication with the controller 202. The memory 206 may be any type of fixed or removable digital storage device and, if needed, a device for reading the digital storage device including, floppy disks and floppy drives, CD-ROM disks and drives, optical disks and drives, hard-drives, EPROM, EEPROM, RAM, ROM and other such devices for storing digital information. The following parameters may stored in the memory 206: magnetic strength (coil working voltage), magnetic field direction (coil on/off sequence), and magnetic field speed (coil time interval) for each layer, mixing time (rotating magnetic field), washing time (constant magnetic field), concentration of magnetic nanoparticles (particle injection time) and final concentrated volume (PBS solution injection time). Alternately, these parameters may be entered into the system 1000 via the user interface 208.

Figure 6:
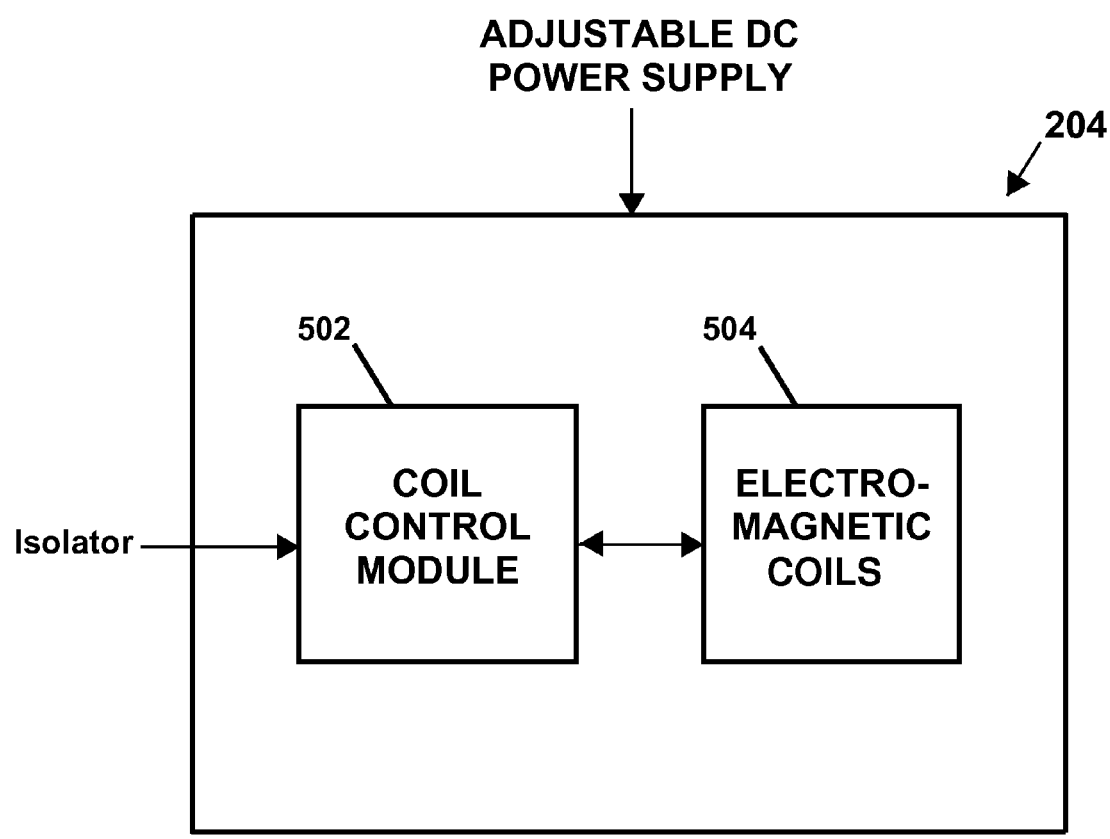
FIG. 6 is a block diagram of a magnetic field subsystem.
Figure 7:
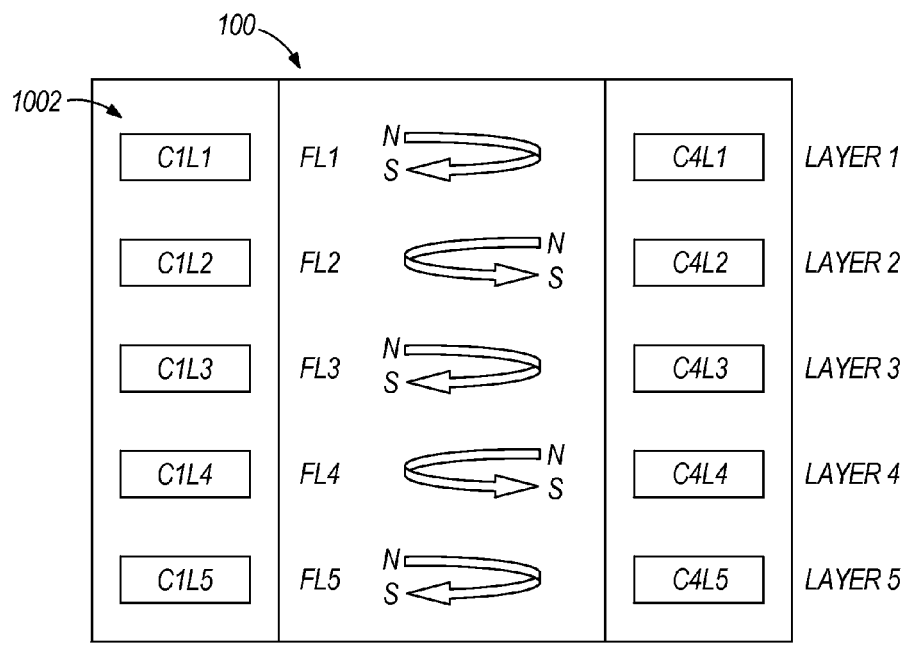
FIG. 7 is a side cross-sectional view of a chamber and magnetic coils of an separation system.
Figure 8:
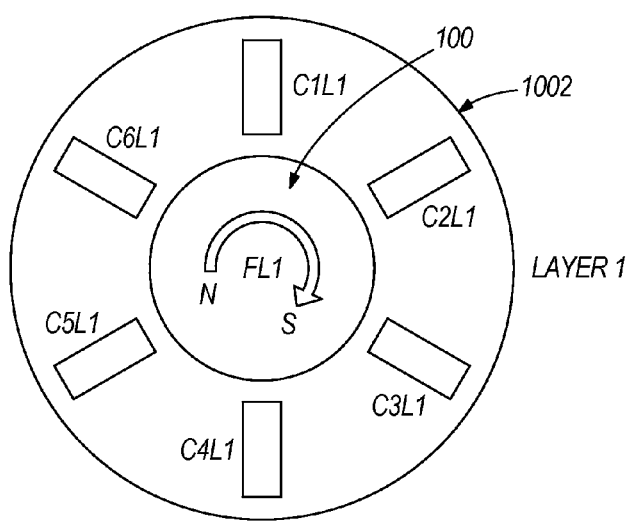
FIG. 8 is a top view of a chamber and magnetic coils of an separation system.

As shown in FIG. 6, the magnetic field subsystem 204 generally includes a coil control module 502 and pairs of electromagnetic coils 504. The coil control module 502 drives the coils 504 according to signals sent by the controller 202. An example of the coils 504 is shown in more detail in FIGS. 7 and 8. FIG. 7 shows a cross-section of the housing 1002 and chamber 100 of the system 1000. The coils (indicated by CxLx) are supported in the housing 1002 generally outside the chamber 100. The coils are arranged in several layers (5 are shown in this example) to provide sufficient magnetic field to cover the depth of the chamber 100. FIG. 8 shows a view of layer 1 of the coils. In this example, there are 6 coils in layer 1 and in the other layers. The coils in each of five layers may be controlled individually by the controller 202 to generate rotating magnetic fields. The direction, speed and strength of the magnetic coils at each layer may be controlled by adjusting the on/off sequence, time interval and voltage. To produce a constant magnetic field, one vertically aligned set of coils is used by applying a voltage to the vertical set when the other coils are off.

The following examples of the methods are meant only to be illustrative and are not intended as limitations on the claims.

Example 1

Capture of *E. coli* with Magnetic Nanoparticles

Culture and plating of bacteria. Frozen stocks of *E. coli* O157:H7 (ATCC 43888), Rifampicin resistant *E. coli* O157:H7 (ATCC 43888), *S. enteritidis* (ATCC 13076), *L. monocytogenes* (FDA 101M 4b), and *Citrobacter freundii* (ATCC 3624) were maintained in Brain Heart Infusion (BHI, with 12% glycerol) broth (Remel Inc., Lenexa, Kans.) at −70° C. All cultures were harvested in BHI broth maintained at 37° C. for 18-22 h. Pure cultures were diluted with 0.01 M, pH 7.4 phosphate-buffered saline (PBS). *E. coli* O157:H7 was surface plated on sorbitol MacConkey (SMAC) agar (Remel Inc., Lenexa, Kans.), which was incubated at 37° C. for 20-22 h. Rifampicin resistant *E. coli* O157:H7 was surface plated on the SMAC agar with 0.3% (wt/vol) rifampicin (Sigma Chemicals Co., St. Louis, Mo.).

Chemicals and reagents. PBS (0.01 M, pH 7.4) was obtained from Sigma-Aldrich (St. Louis, Mo.). Bovine serum albumin (BSA, EM Science, Gibbstown, N.J.), 0.5% (wt/vol) was prepared in PBS as a blocking buffer (PBS BSA). PBS (0.05 M, pH 7.0) was used for serial dilution of bacteria before surface plating. All solutions were prepared with deionized water from Millipore (Milli-Q, 18.2 MΩ·cm, Bedford, Mass.). PBS Tween-20 0.05% (wt/vol) (PBST, Sigma-Aldrich, St. Louis, Mo.) was used for washing immunomagnetic particles.

Nanoparticles and microbeads. Magnetic nanoparticles (average diameter of 145 nm, Captivate™ ferrofluid streptavidin, 0.5 mg Fe/mL) conjugated with streptavidin were obtained from Molecular Probes Inc. (Eugene, Oreg.). Magnetic nanoparticles (MN) have more than 85% of oxide as $Fe_3O_4$, approximately 80% wt/wt of magnetite, and approximately $4 \times 10^{11}$ particles/mg Fe. Based on these values, the number of magnetic nanoparticles per µL was estimated as $1.6 \times 10^8$. Affinity purified polyclonal goat antibodies against *E. coli* (specific for O and K antigens), conjugated with biotin were obtained from Biodesign International (Saco, Me.). The concentration of stock solution of biotin labeled antibodies was 4-5 mg/mL. A 1:10 dilution of the antibodies was prepared in PBS (0.01 M, pH 7.4) before use. This dilution of the biotin conjugated anti-*E. coli* was used for all tests. Magnetic microbeads (MMBs, 2.8 µm diameter) coated with affinity purified polyclonal antibodies against *E. coli* O157:H7 were obtained from Dynal, Inc. (Lake Success, N.Y.).

Preparation of magnetic nanoparticle-antibody conjugates. Magnetic nanoparticle-antibody conjugates (MNCs) were prepared in 1.7 mL sterile polypropylene centrifuge tubes. Biotin labeled polyclonal goat anti-*E. coli* antibodies (10 µL) were continuously mixed with streptavidin-coated magnetic nanoparticles (20 µL) in 250 µL PBS BSA at 7 RPM on a variable speed rotator (ATR, Laurel, Md.) for 35 min at room temperature.

Capture efficiency calculations. Capture efficiency (CE), defined as the percentage fraction of the total bacteria retained on the surface of the beads, may be calculated using two methods: one is based on the cells bound to immunomagnetic particles and other is based on the cells unbound to immunomagnetic particles or left in the supernatant. In both cases conventional plating method was used to determine the binding kinetics of the immunomagnetic particles. The following two equations were used:

For CE based on cells bound to immunomagnetic particles $$CE(\%) = \frac{C_b}{C_o} \times 100 \tag{1}$$

For CE based on cells unbound to immunomagnetic particles $$CE(\%) = \left(1 - \frac{C_u}{C_o}\right) \times 100 \tag{2}$$

where, $C_o$ is the total number of cells present in the sample (CFU/mL); $C_b$ is the number of cells bound to immunomagnetic particles (CFU/mL); $C_u$ is the number of cells unbound to immunomagnetic particles (CFU/mL).

Figure 9:
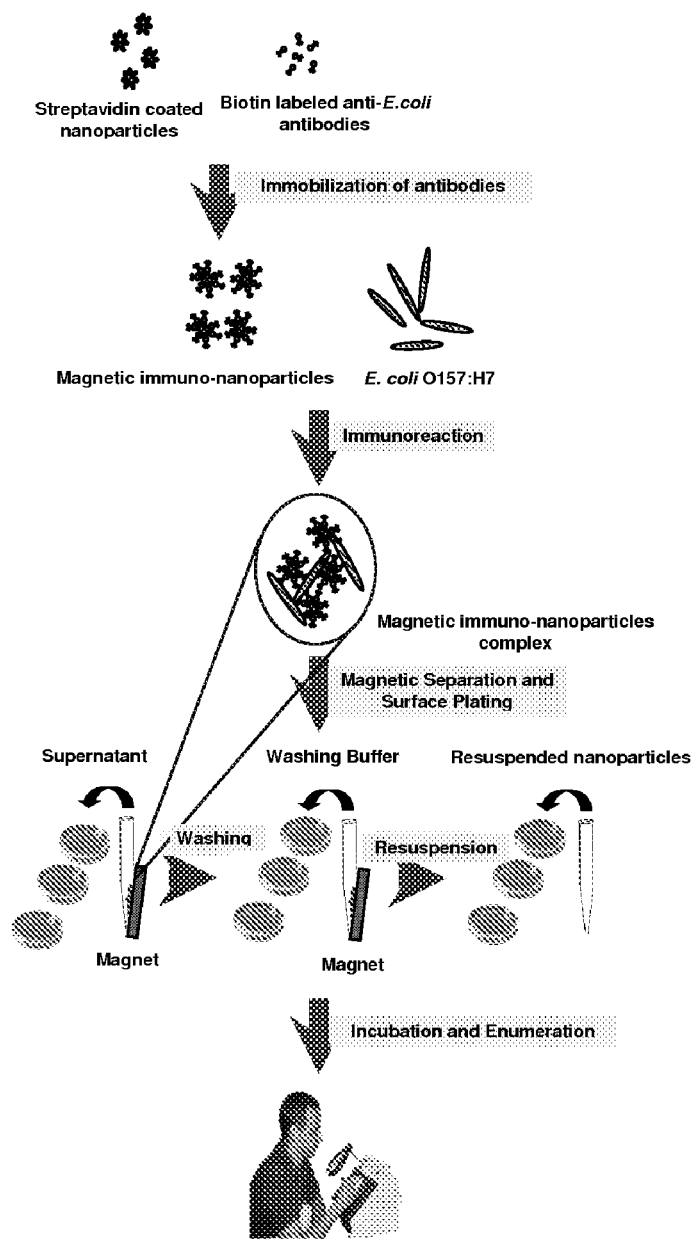
FIG. 9 is a schematic diagram of one embodiment of the process of immunomagnetically separating a contaminant with a magnetic nanoparticle.

Assay procedure. A representative assay procedure is shown in FIG. 9. Serial dilutions of *E. coli* O157:H7 were prepared in PBS (0.01 M, pH 7.4) buffer. Immunoreaction between immunomagnetic particles and bacteria and magnetic separation was followed by plating to enumerate bacteria. For all tests a sample size of 0.5 mL was used and therefore CFU/0.5 mL was used as the unit in presenting bacterial concentration. Four immuoreaction times (15, 30, 45, and 60 min) and five bacterial concentrations ($10^0$, $10^1$, $10^3$, $10^5$, and $10^7$ CFU/0.5 mL) were used.

Immunoreaction was carried out by mixing 20 μL of immunomagnetic particles with 0.5 mL of a sample at a given cell concentration at 10 RPM with a variable speed rotator. After the indicated immunoreaction time, tubes were removed from the rotator and the immunomagnetic particles were separated from the supernatant with a magnetic particle concentrator (MPC, Dynal Inc., Lake Success, N.Y.). An aliquot of 0.1 mL from supernatant was surface plated for bacterial enumeration after appropriate dilution. A total of 0.5 mL of PBST was used to wash immunomagnetic particles two times. An aliquot of 0.1 mL from supernatants from each washing solution was surface plated after appropriate dilution. Finally, immunomagnetic particles were resuspended in 0.5 mL of PBS BSA and 0.1 mL was used for plating after appropriate dilution. Each sample was plated in triplicate.

To control for *E. coli* O157:H7 growth during the test a corresponding sample of *E. coli* O157:H7 in PBS BSA was left for 60 min at room temperature (22° C.) and plated onto SMAC agar plates. The plating result was compared with the initial cell number of *E. coli* O157:H7 in the same sample.

For cell concentrations less than or equal to $10^1$ CFU/0.5 mL of *E. coli* O157:H7, after immunoreaction and separation, all supernatant (0.5 mL) was plated on a set of five SMAC agar plates. The washing buffer was also plated on five SMAC agar plates. Similar steps were applied for the resuspended immunomagnetic particle-antibody-bacteria complex. Finally, all five plates were counted for the total number of colony-forming units in a particular test. The values of CE were calculated based on equations 1 and 2. Initial cell number per mL in these samples was determined by surface plating 0.1 mL of the sample on each of ten agar plates and adding cell numbers on all ten plates to obtain an initial bacterial count per mL.

Figure 10:
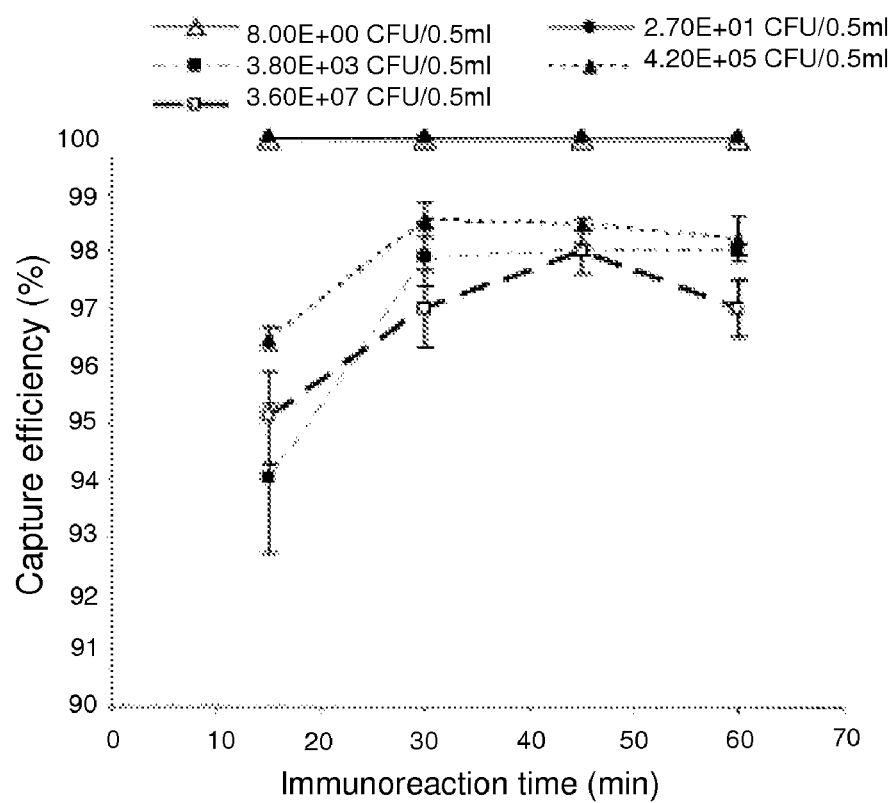
FIG. 10 shows the capture efficiency of magnetic nanoparticle-antibody conjugates against several concentrations of *E. coli* O157:H7 over a range of immunoreaction times.

Capture efficiency of magnetic nanoparticle conjugates against *E. coli* O157:H7. To obtain an accurate bacterial count, 1 mL aliquots at each cell concentration were prepared and divided equally into control and test samples. The controls were diluted and plated to obtain an accurate number of bacteria for each inoculum ($C_o$). Test samples were mixed with MNCs ($C_b$). After magnetic separation, supernatant was plated to determine the fraction of bacteria not bound with immunomagnetic particles ($C_u$). CE was calculated based on the comparison of the bacterial count of controls and samples using equations 1 and 2. Table 1 shows the relationship between cell concentrations and the fraction of bacteria captured by MNCs after a 15 min immunoreaction time. For $8.0 \times 10^0$, $2.7 \times 10^1$, $3.8 \times 10^3$, $4.2 \times 10^5$, and $3.6 \times 10^7$ CFU/0.5 mL of *E. coli* O157:H7, the CE values were 100%, 100%, 94%, 96%, and 95%, respectively. As shown in FIG. 10, for all immunoreaction times tested the CE was greater than 94% for the entire range of *E. coli* O157:H7 concentrations tested.

TABLE 1

Capture efficiency of magnetic nanoparticles conjugates against $8.0 \times 10^0$, $2.7 \times 10^1$, $3.8 \times 10^3$, $4.2 \times 10^5$, and $3.6 \times 10^7$ CFU/0.5 ml of *E. coli* O157:H7 for 15 min of immunoreaction time.

| E. coli O157:H7 concentration | Mean and STD[a] of bacteria captured by 20 μl of nanoparticles (CFU) | | Fraction of total bacteria captured by the nanoparticles (%) | |
|---|---|---|---|---|
| (CFU/0.5 ml) | Supernatant[b] | Nanoparticles[c] | Supernatant[b] | Nanoparticles[c] |
| $8.0 \times 10^0$ | $0 \pm 0$ | $7.0 \pm 2.4$ | 100 | 88 |
| $2.7 \times 10^1$ | $0 \pm 0$ | $2.5 \times 10^1 \pm 3.0$ | 100 | 94 |
| $3.8 \times 10^3$ | $3.6 \times 10^3 \pm 4.9 \times 10^1$ | $3.5 \times 10^3 \pm 2.9 \times 10^1$ | 94 | 92 |
| $4.2 \times 10^5$ | $4.1 \times 10^5 \pm 1.0 \times 10^3$ | $3.1 \times 10^5 \pm 1.2 \times 10^5$ | 96 | 73 |
| $3.6 \times 10^7$ | $3.4 \times 10^6 \pm 5.6 \times 10^5$ | $2.6 \times 10^7 \pm 6.1 \times 10^6$ | 95 | 74 |

[a]3 replicates were taken for all readings.
[b]Capture efficiency was calculated based on the bacteria present in the supernatant.
[c]Capture efficiency was calculated based on the bacteria bound to magnetic nanoparticles.

As shown in Table 1 and FIG. 10, CE was greater than 94% for the separation of *E. coli* O157:H7 from $10^0$ to $10^7$ CFU/0.5 mL even with an immunoreaction time of 15 min. Thus, a 15 min immunoreaction time was used in all further tests. CE calculations based on surface plate counts of cells bound to nanoparticles (equation 1) were generally less than those based on unbound cells in the supernatant (equation 2). Scanning electron micrographs show cluster formation of MNCs and MMBs in the presence of *E. coli* O157:H7 when a magnetic field is applied. The CE values calculated based on the number of cells bound to the magnetic nanoparticles may be underestimated because clusters of cells and particles may be formed. The result would be the formation of only one colony on the plate, causing an underestimation of separation of bacteria by magnetic particles. Thus CE calculations based on plating of unbound cells in the supernatant presents useful quantitative information on separation of bacteria by magnetic particles when the initial amount of bacteria is known.

Example 2

Comparison of Magnetic Nanoparticle-Antibody Conjugates with Immunomagnetic Microbeads For comparison, magnetic microbeads (MMBs) were used in parallel with MNCs, following the same procedure. For MMBs, the immunoreaction was carried out by mixing 10 μL of MMBs with 0.5 mL of a sample containing *E. coli* O157: H7 at a given cell concentration by rotating at 10 RPM with a variable speed rotator.

Figure 11:
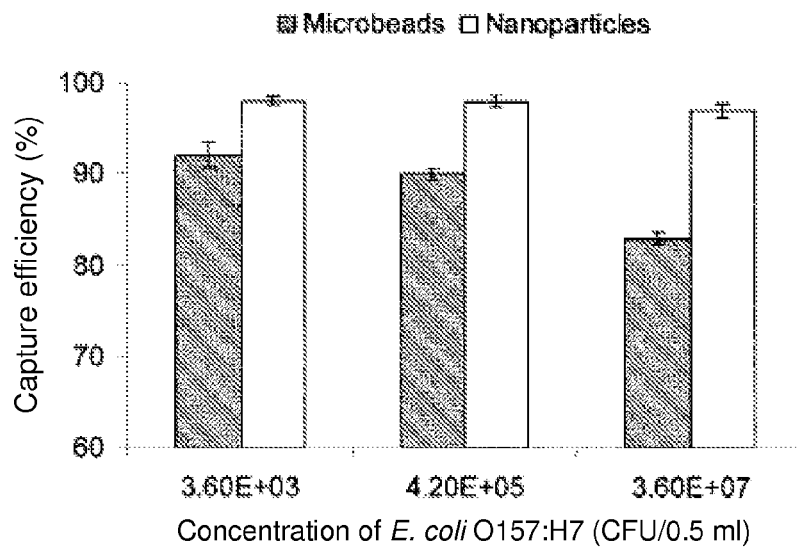
FIG. 11 shows a comparison of the CE of MNCs and MMBs for *E. coli* O157:H7. A) shows the effect of *E. coli* concentration. B) shows the effect of several immunoreaction times.
Figure 11:
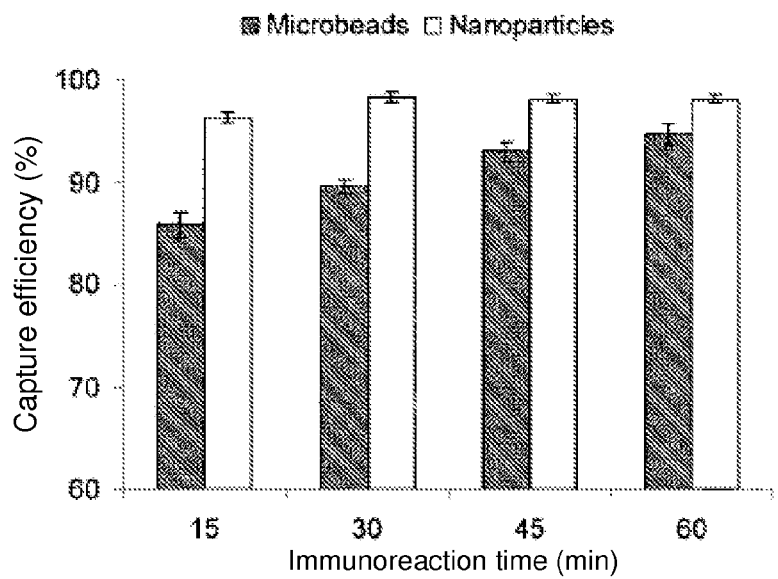

MNCs resulted in significantly higher capacity (CE values) to separate *E. coli* O157:H7 as compared to MMBs for all combinations of three levels of cell numbers with four immunoreaction times. FIG. 11a shows CEs of both MNCs and MMBs for detection of E. coli O157:H7 at 3 concentrations ($10^3$, $10^5$, $10^7$ CFU/0.5 mL) with an immunoreaction time of 30 min. MMBs showed a decrease in CE with an increase in concentration of bacteria. CEs of MMBs were 92%, 90%, and 83% for $3.6 \times 10^3$, $4.2 \times 10^5$, and $3.5 \times 10^7$ CFU/0.5 mL of E. coli O157:H7, respectively. MNCs showed CEs of 98%, 98%, and 97% for $3.6 \times 10^3$, $4.2 \times 10^5$, and $3.5 \times 10^7$ CFU/0.5 mL, respectively, and showed no correlation between CE of bacteria and increasing concentrations of E. coli O157:H7.

FIG. 11b shows CEs of both MNCs and MMBs using different immunoreaction times (15, 30, 45, and 60 min) in the detection of $3.6 \times 10^5$ CFU/0.5 mL of E. coli O157:H7. The CE values of MNCs were greater than 96% with all four immunoreaction times, while the CE values of MMBs increased with increasing immunoreaction time. The CE values with the MNCs increased from 96.3% to 98.4% when the immunoreaction time increased from 15 min to 30 min. After 30 min, CE remained at almost 98% for longer immunoreaction times. Hence, MNCs did not show time-dependant increases in the separation of E. coli O157:H7 after 30 min immunoreaction time. No significant growth ($p > 0.05$) was observed when $3.5 \times 10^5$ of E. coli O157:H7 present in PBS BSA was incubated at room temperature for 60 min.

In this study, the high binding capacity of MNCs resulted in a CE of 96.3% for $3.6 \times 10^5$ CFU/0.5 mL of E. coli O157:H7 within 15 min of immunoreaction time. MNCs were found to separate approximately 10% more E. coli O157:H7 as compared to magnetic microbeads in 15 min of immunoreaction time.

Example 3

Detection of E. coli in Ground Beef

Food sample preparation and enrichment. Commercial ground beef was purchased from a local supermarket. Two types of samples were prepared for ground beef: one with enrichment for low cell concentrations ($10^0$ and $10^1$ CFU/mL) in tryptic soy broth (TSB, EM Science, Gibbstown, N.J.), and the other without enrichment for higher concentrations ($10^3$ to $10^7$ CFU/mL) in buffered peptone water (BPW, Remel Inc., Lexena, Kans.). For both cases, 25 grams of ground beef was homogenized with 225 mL of 0.1% BPW or TSB in a Whirl-pak plastic bag using a laboratory stomacher 400 (Seward, UK) for 2 min. After stomaching, food samples were inoculated with decimally diluted cultures of E. coli O157:H7. For enrichment, 1 mL of $8 \times 10^1$ CFU/mL and $4 \times 10^2$ CFU/mL of E. coli O157:H7 was added to 9 mL of TSB homogenized ground beef samples, and incubated at 37° C. for 6 h. For samples without enrichment, 1 mL of E. coli O157:H7 ranging from $6.0 \times 10^4$ CFU/mL to $3.4 \times 10^8$ CFU/mL was inoculated into 9 mL of BPW homogenized ground beef samples. For $10^0$, $10^1$, and $10^3$ CFU/mL concentrations, rifampicin resistant E. coli O157:H7 was used to avoid the growth of naturally present bacteria from ground beef samples on plates. For both types of food sample preparation, samples without added E. coli O157:H7 and rifampicin resistant E. coli O157:H7 were used as a negative control and were surface plated on SMAC and R-SMAC (rifampicin-containing SMAC) agar, respectively, and incubated at 37° C. for 18-22 h.

To observe the effect of food components on CE of MNCs for E. coli O157:H7 in ground beef samples, two set of tests were compared: one on the sample collected after stomaching only; and the other on the sample after stomaching, filtration with cheese cloth and centrifugation (two times at 250×g for 15 min) in order to separate large size particles present in the ground beef stomaching water. E. coli O157:H7 was added after sample preparation. Steps for immunoreaction and separation were the same as described before. Only $10^3$ to $10^7$ CFU/0.5 mL of E. coli O157:H7 were compared in order to avoid enrichment step.

Figure 12:
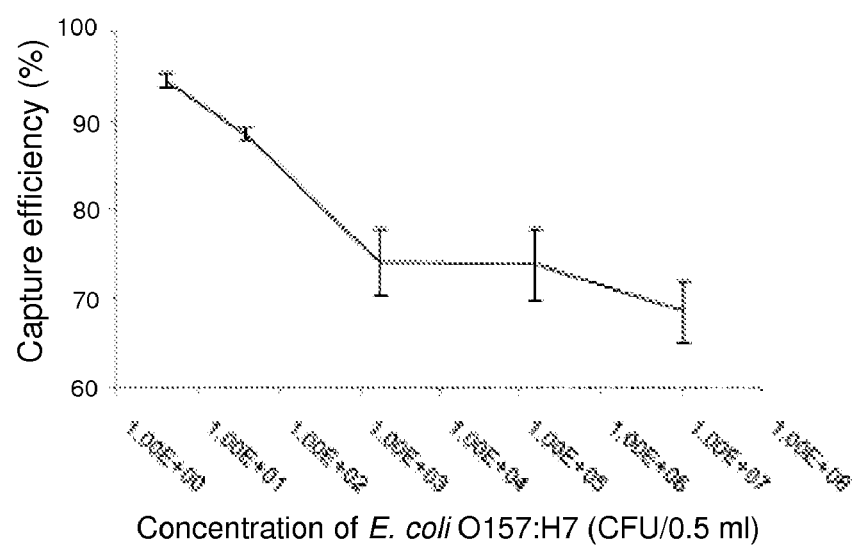
FIG. 12 shows the capture efficiency of magnetic nanoparticle-antibody conjugates in the capture of *E. coli* O157:H7 in ground beef samples prepared by stomaching only.

Capture efficiency of magnetic nanoparticles conjugates for E. coli O157:H7 in ground beef samples. E. coli O157:H7 and rifampicin resistant E. coli O157:H7 were not found in uninoculated ground beef samples used in this study, based on plating of the samples on SMAC and R-SMAC agars. FIG. 12 shows CE values for the range of concentration from $4 \times 10^0$ to $1.7 \times 10^7$ CFU/0.5 mL of E. coli O157:H7 in the ground beef sample prepared with stomaching only. For $4.0 \times 10^0$ and $4.0 \times 10^1$ CFU/0.5 mL of E. coli O157:H7, the mean values of CE were 94.5% and 88.5%, respectively. In our experiments, during enrichment steps E. coli O157:H7 inoculated at $8.0 \times 10^0$ and $8.0 \times 10^1$ CFU/mL reached to $1.4 \times 10^3$ and $4.7 \times 10^3$ CFU/mL in ground beef samples, respectively. Without any enrichment, higher concentrations of E. coli O157:H7 gave mean CE values of 74%, 73.9%, and 68.5% for $1.8 \times 10^3$, $1.6 \times 10^5$, and $1.7 \times 10^7$ CFU/0.5 mL of E. coli O157:H7, respectively.

For $10^3$ to $10^7$ CFU/0.5 mL of E. coli O157:H7 inoculated in the ground beef samples, presence of larger sized food particles in the stomached samples reduced the CE values by 6% to 12%, when compared with the CE values obtained in the samples prepared with stomaching, filtration and centrifugation (data not shown). The most probable reason for such observation may be the binding of E. coli O157:H7 with food matrix or the entrapment of nanoparticles in larger sized organic particles present in the ground beef sample that was not filtered or centrifuged.

Example 4

Detection of E. coli in Milk Samples

Figure 13:
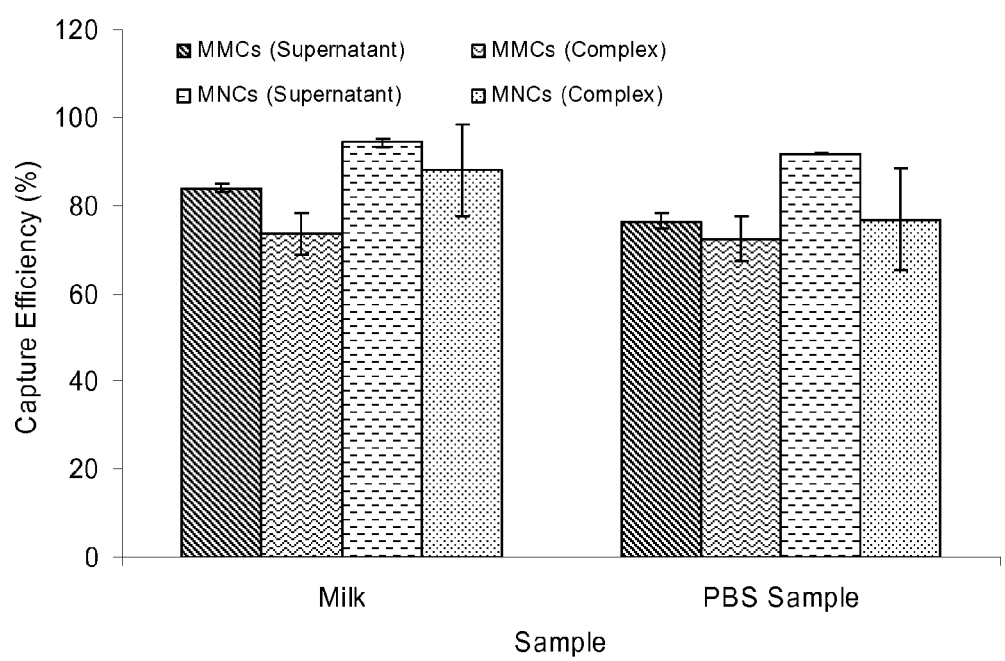
FIG. 13 shows the capture efficiency of magnetic nanoparticle-antibody conjugates and magnetic microbead-antibody conjugates for the separation of *E. coli* O157:H7 from milk.

Commercial milk was purchased from a local supermarket and utilized in experiments similar to those described in Example 3 above. FIG. 13 shows the capture efficiency of MMBs and MNCs in PBS and milk. Higher capture efficiency values were observed for both immunomagnetic particles for the separation of E. coli O157:H7 in milk samples as compared to PBS buffer. This may be attributed to the fact that milk contains casein and other proteins, which act as a blocking agent. The capture efficiency of the MNCs was 94.5% in milk and 91.7% in PBS. The capture efficiency of the magnetic MMBs was only 83.9% in milk and only 76.5% in PBS. Statistical analysis showed that the capture efficiency of MNCs for E. coli O157:H7 in milk and PBS samples were not significantly different ($p > 0.05$). The capture efficiency of MMBs for E. coli O157:H7 in milk and PBS samples were significantly different ($p < 0.05$). In addition the capture efficiencies of the MMBs were significantly less than those of the MNCs ($p < 0.05$).

Example 5

Specificity for the Target Contaminant

Non-specific binding of MNCs was tested for three non-target bacteria—S. enteritidis, L. monocytogenes, and C. freundii. All three non-target bacteria were added with rifampicin resistant E. coli O157:H7 in ground beef samples as described in Example 3. The known number of non-target bacteria added with 2.5×10⁴ CFU/0.5 mL of *E. coli* O157:H7 were approximately 10⁶ CFU/0.5 mL. Binding of MNCs against target and non-target bacteria was tested by the plating method described earlier. Inoculum levels of non-target bacteria were estimated by plating onto TSA agar plates, and rifampicin resistant *E. coli* O157:H7 was grown on R-SMAC agar plates. Uninoculated ground beef samples were plated onto SMAC and R-SMAC agar plates to check the natural presence of *E. coli* O157:H7 and rifampicin resistant *E. coli* O157:H7 in the beef samples. The immunoreaction time was 15 min.

CE of MNCs for 2.4×10⁴ CFU/0.5 mL of *E. coli* O157:H7 in ground beef was 94% when no non-target bacteria were added to the ground beef sample. When 2.4×10⁴ CFU/0.5 mL of *E. coli* O157:H7 was mixed with 10⁶ CFU/0.5 mL of each *S. enteritidis, L. monocytogenes*, and *C. freundii* in ground beef for the specific separation of target *E. coli* O157:H7 from food samples, the CE value was found to decrease by 12%. Therefore, MNCs showed some affinity for these non-target bacteria and other competing microflora in the ground beef samples. However, a substantial amount (82%) of *E. coli* O157:H7 was still separated by MNCs even in the presence of a large number of non-target bacteria within 15 min. Uninoculated ground beef samples did not show presence of *E. coli* O157:H7 or rifampicin resistant *E. coli* O157:H7 on SMAC or R-SMAC agar plates, respectively.

Example 6

Effect of Mixing During Immunoreaction on Capture Efficiency

To determine the effect of mixing on CE of MNCs and MMBs, two tests were performed—one with mixing in a variable speed rotator at 10 RPM as in the prior examples and the other without mixing. PBS BSA was used with 8.9×10³ CFU/mL of *E. coli* O157:H7 in milk samples with a 15 min immunoreaction time. All other steps for the calculation of CE were same as described in the previous examples.

Figure 14:
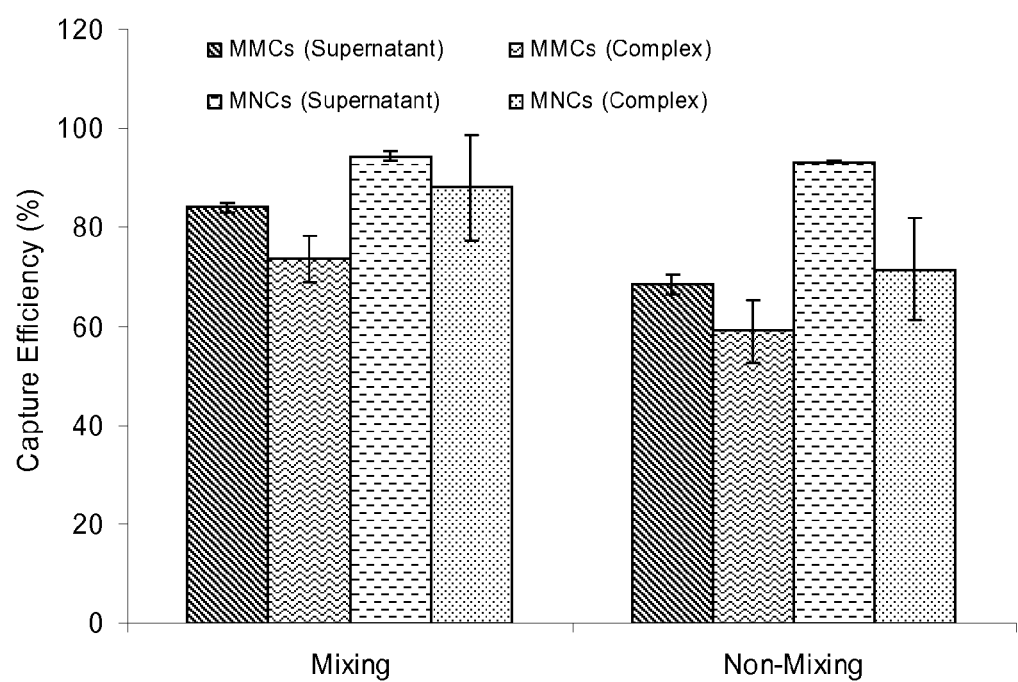
FIG. 14 shows the effect of mixing during the immunoreaction on the capture efficiency of magnetic nanoparticle-antibody conjugates and magnetic microbead-antibody conjugates for the separation of *E. coli* O157:H7 from milk.

FIG. 14 shows the effect of mixing on CE of MNCs and MMBs for 8.9×10³ CFU/mL of *E. coli* O157:H7 in milk samples. MNCs showed CE values of 94% and 93% for the samples obtained by mixing and non-mixing, respectively. There was no significant difference between these two CE values ($p>0.05$). Thus, results indicated that there was no effect of mechanical mixing on the capture of bacteria by MNCs. There was a significant effect ($p<0.05$) of mixing on the capture of bacteria by MMBs, as shown by the CE values of 84% and 68% for the samples prepared by mixing and non-mixing, respectively. Similar results were obtained with ground beef samples. The CE values in ground beef samples for MNCs were 95% and 94% for samples obtained by mixing and non-mixing, respectively ($p>0.05$). The CE values for MMBs in ground beef samples with MMBs were 62% and 52% for samples obtained by mixing and non-mixing, respectively ($p<0.05$). Therefore, magnetic nanoparticles offer distinct advantages in terms of no mixing required for the immunoreaction between magnetic particles and bacteria and thus may be a good choice for microfluidic applications.

Example 7

Impedance Biosensing Method Based on Magnetic Nanoparticle-Antibody Conjugates for Detection of *E. coli* in Ground Beef An impedance biosensing method based on MNCs and interdigitated microelectrodes was developed and evaluated for rapid detection of *E. coli* O157:H7 in ground beef samples based on Example 3. The spectrum of the magnitude of impedance and phase angle was measured for a range of frequency from 10 Hz to 1 MHz in the presence of 0.1 M mannitol solution without any electrode surface modification or use of redox. MNCs were prepared by immobilizing biotin-labeled polyclonal goat anti-*E. coli* antibodies onto streptavidin-coated magnetic nanoparticles and were used for the specific separation of *E. coli* O157:H7 from ground beef samples and concentrating them to a very small volume suitable for detection with the interdigitated microelectrodes. It was also found that the sensitivity of impedance biosensing method was improved by concentrating MNCs bound cells in the active region of IME above the surface of electrodes with the help of a magnetic field.

Figure 15:
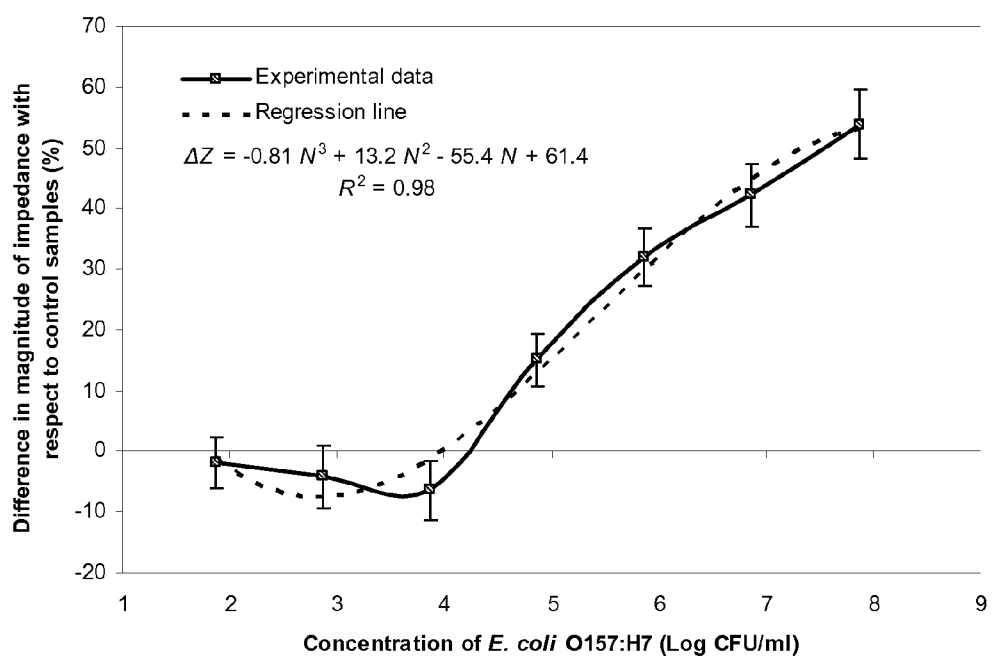
FIG. 15 shows the difference in the magnitude of impedance of samples containing a range of *E. coli* O157:H7 concentrations as compared to control samples containing no bacteria in PBS.

FIG. 15 shows the difference in magnitude of impedance ($\Delta Z$) with respect to the control sample for different concentrations (N) of *E. coli* O157:H7 from 7.4×10¹ to 7.4×10⁷ CFU mL⁻¹ at 40 KHz. Positive values indicate a decrease in impedance (increase in conductivity) and negative values indicate an increase in impedance (decrease in conductivity). The results clearly demonstrated that concentrations of *E. coli* O157:H7 greater then 7.4×10⁴ CFU mL⁻¹ resulted in an increase in conductivity of the medium. The application of magnetic field was successfully used for the concentration of cells in the active region of electrodes surface and was sufficient to cause an increase in conductivity in the range of 15 to 54% for the concentrations of *E. coli* O157:H7 from 7.4×10⁴ to 7.4×10⁷ CFU mL⁻¹. Concentrations of *E. coli* O157:H7 less than 7.4×10⁴ CFU mL⁻¹ resulted in an average negative change, hence decrease in conductivity, of the medium, however they were not significantly different from the impedance of a control sample ($P>0.05$). Probably the low numbers of cells were not sufficient to cause increase in conductivity with respect to the background. Thus impedance measurement was successfully used for the detection of a range of *E. coli* O157:H7 from 7.4×10⁴ to 7.4×10⁷ CFU mL⁻¹. The regression equation for the difference in magnitude of impedance with respect to control sample for the concentrations of *E. coli* O157:H7 from 7.4×10¹ to 7.4×10⁷ CFU mL⁻¹ was $\Delta Z = -0.81 N^3 + 13.2 N^2 - 55.4 N + 61.4$ with $R^2 = 0.98$, where $\Delta Z$ is the difference in the magnitude of impedance with respect to control sample in percentage and N is the concentration of *E. coli* O157:H7 in CFU mL⁻¹. Combination of IMS, impedance measurement and influence of magnetic field on the concentration of cells in the active region above the electrodes surface showed promising results for the detection of a minimum of 7.4×10⁴ CFU mL⁻¹ of *E. coli* O157:H7.

Figure 16:
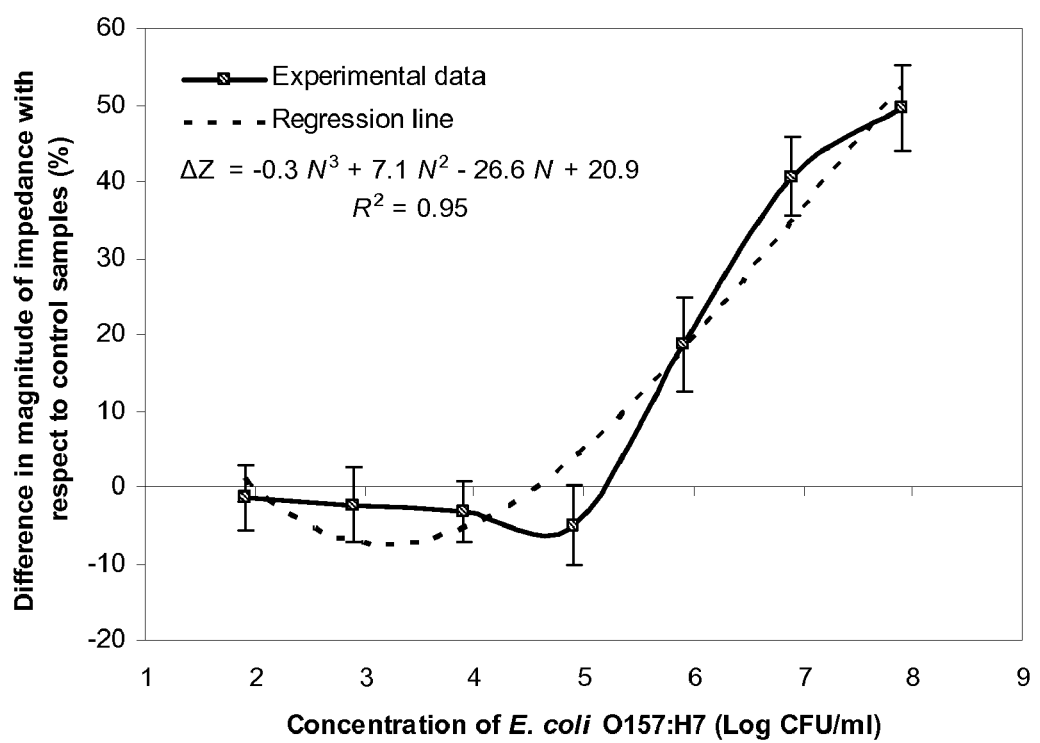
FIG. 16 shows the difference in the magnitude of impedance of samples containing a range of *E. coli* O157:H7 concentrations as compared to control samples containing no bacteria in ground beef.

FIG. 16 shows the difference in magnitude of impedance ($\Delta Z$) for the concentrations of *E. coli* O157:H7 (N) from 8.0×10¹ to 8.0×10⁷ CFU mL⁻¹ present in ground beef samples at 40 KHz. The graph clearly demonstrates that a minimum concentration of 8.0×10⁵ CFU mL⁻¹ of *E. coli* O157:H7 present in ground beef caused a significant ($P<0.05$) positive change in magnitude of impedance (increase in conductivity) with respect to control samples as compared to 7.4×10⁴ CFU mL⁻¹ of *E. coli* O157:H7 present in PBS buffer. Impedance biosensing coupled with MNCs was successfully used for the detection of a range of *E. coli* O157:H7 from 8.0×10⁵ to 8.0×10⁷ CFU mL⁻¹ in ground beef samples. The impedance values for the samples with 8.0×10¹ to 8.0×10⁴ CFU mL⁻¹ of *E. coli* O157:H7 were not significantly different ($P>0.05$) from the impedance values of the control samples. The regression equation for the difference in magnitude of impedance with respect to control sample for the cell numbers from 8.0×10¹ to 8.0×10⁷ CFU mL⁻¹ of *E. coli* O157:H7 was $\Delta Z = -0.3 N^3 + 7.1 N^2 - 26.6 N + 20.9$ with $R^2 = 0.95$, where $\Delta Z$ is difference in the magnitude of impedance with respect to control samples in percentage and N is the concentration of *E. coli* O157:H7 in CFU mL$^{-1}$.

Example 8

QCM Biosensor Combined with Immunomagnetic Nanoparticles for Detection of *E. coli* O157:H7

Figure 17:
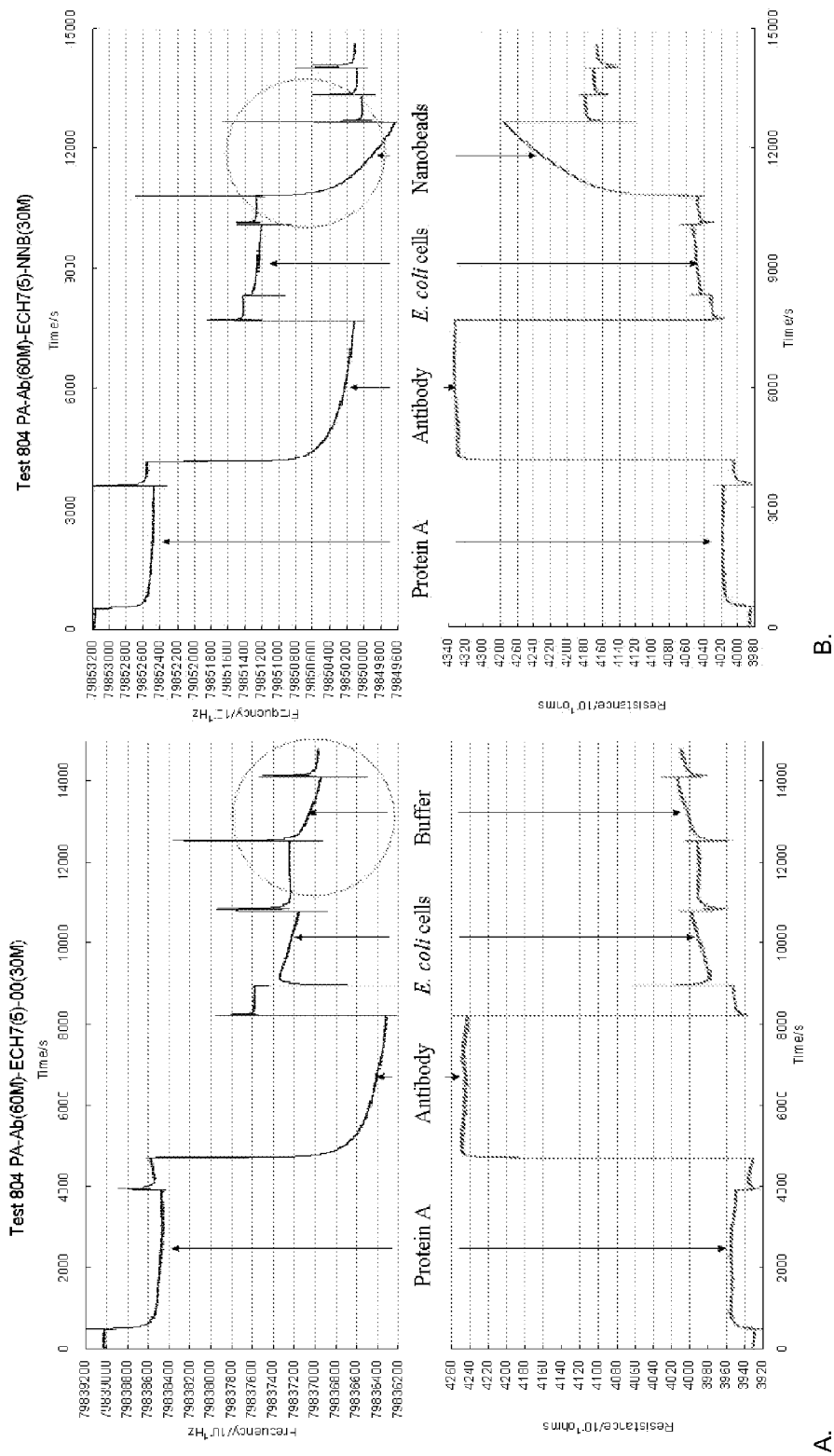
FIG. 17 shows the frequency and resistance measured in the QCM biosensor for *E. coli* O157:H7 in a sample without the addition of magnetic nanoparticles (a) and with the nanoparticles (b).

QCM (quartz crystal microbalance) biosensors have been studied for rapid detection of bacterial pathogens, but are limited by their sensitivity (usually more than 1,000 cfu/mL). Immuno-nanoparticles may be used in conjunction with QCM biosensors for the amplification of bacterial signals. MNCs were prepared as in the previous examples by immobilizing biotin labeled anti-*E. coli* antibodies onto streptavidin-coated nanoparticles (140 nm diameter). The immuno-nanoparticles were first mixed with ground beef to bind the target, *E. coli* O157:H7, and then separated from the food product, as described earlier. Then the complexes of immunonanoparticles and *E. coli* O157:H7 cells were pumped into a flow cell. In the flow cell, an AT-cut quartz crystal's Au electrode was immobilized with anti-*E. coli* O157:H7 antibodies using a self-assembled monolayer method. After 30 min immunoreaction, both resonant frequency and motional resistance were measured. The result, depicted in FIG. 17, showed that with the amplification step, the change in both frequency and resistance was more than doubled in comparison to that without amplification. Inclusion of the amplification step allowed the QCM biosensor to detect $10^2$ cfu/mL, as depicted in Table 2.

conjugated to the monoclonal antibody and 50 µL of nanoparticles bound to BSA-atrazine (competitor complex). The combination was mixed for 30 minutes with gentle rotation at 10 rpm at room temperature. The combination was then subjected to a magnetic field to separate the competitor complexes bound to the antibody-QD from the starting or control material. The competitor complexes were washed three times with PBS to remove any unbound antibody-QD complexes. If atrazine was present in the starting material, this atrazine would compete with the competitor complex for binding the antibody-QD and would be expected to reduce the amount of QD-antibody binding to the competitor complex and thus reduce the fluorescence intensity of the competitor complex. Finally, the competitor complexes were resuspended in 200 µL PBS and the fluorescence emission of the competitor complex was detected at 606.46 nm using an Ocean Optics USB 2000 fluorescence detector at a selected integration time of either 64 ms or 128 ms.

Figure 18:
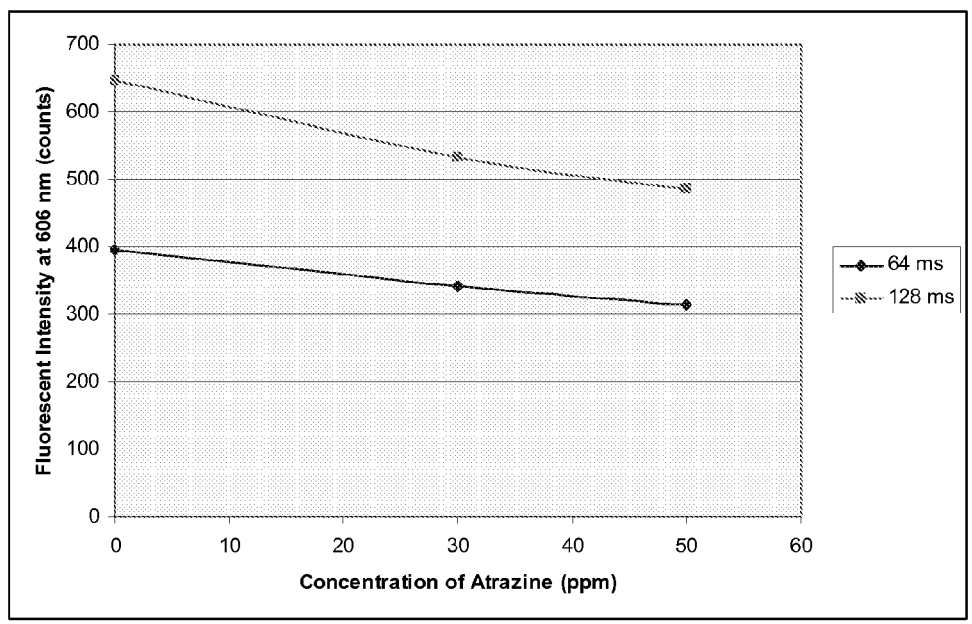
FIG. 18 shows the result of atrazine detection using the competitive assay based on magnetic-nanoparticles and quantum dots conjugated to antibodies as biolabels.

The results of this experiment are shown in Table 3 and FIG. 18. Table 3 contains the fluorescence intensity data from a representative experiment comparing a control sample that contained no atrazine to samples containing atrazine at 30 ppm or 50 ppm and FIG. 18 is a graphic representation of the same data. The experiment demonstrated that the antibody-QD complex was capable of binding the competitor complex when no atrazine was present in the control material as shown by the relatively high level of fluorescence intensity.

TABLE 2

Change in frequency and resistance in preparation of the electrode and detection of
*E. coli* O157:H7 using a QCM immunosensor with immunomagnetic-nanobeads

| | | | | Cell number of *E. coli* O157:H7 (cfu/mL) | | | | | | |
|---|---|---|---|---|---|---|---|---|---|---|
| Measurement | Protein A | Antibody | BSA | 0 | $10^1$ | $10^2$ | $10^3$ | $10^4$ | $10^5$ | $10^6$ |
| ΔF (Hz) | 16.1 | −116.2 | 4.6 | 2.3 | −1.2 | −3.5 | −13.9 | −25.5 | −46.7 | −73.8 |
| ΔR (Ω) | −1.5 | 2.1 | −0.7 | −0.7 | 0.5 | 4.2 | 10.5 | 41.7 | 60.7 | 87.2 |

Example 9

Competitive Labeling Method for the Detection of Atrazine

Reagents. Monoclonal antibody to atrazine was obtained from Biodesign International (Saco, Me.). Atrazine (Pestanol®) was purchased from Sigma-Aldrich Laborchemikalien (Seelze, Germany). Streptavidin conjugated nanoparticles (Captivate™ ferrofluid streptavidin) were obtained from Molecular Probes, Inc. (Eugene, Oreg.). Quantum dots (QD) were supplied by the Quantum Dot Corp. (Hayward, Calif.) and the Qdot Antibody Conjugation kit was used to couple the antibody to the quantum dot.

Preparation of the competitor nanoparticle coupled to atrazine. Atrazine was coupled to BSA (HOW?). The resulting BSA-atrazine was biotinylated and then mixed with streptavidin coated nanoparticles. The nanoparticles were separated from unbound BSA-atrazine by magnetic separation followed by three washes to remove any unbound BSA-atrazine.

Competitive assay procedure. The starting material, containing known dilutions of atrazine, and control material, containing no atrazine, were mixed with 10 µL of 1.2 µM QD

TABLE 3

Results of the test on detection of atrazine residue using the
biosensing method based on quantum dot biolabels and
magnetic nanoparticle immunoseparation

| | Fluorescent Intensity at 606 nm (counts) | |
|---|---|---|
| Concentration of Atrazine (ppm) | Integrated Time 64 ms | Integrated Time 128 ms |
| 0 | 394.7 | 645.7 |
| 30 | 342.6 | 531.8 |
| 50 | 314.3 | 486.1 |

When atrazine was present in the starting material, the fluorescence intensity associated with the competitor complex was reduced. For example, when 50 ppm atrazine was present in the starting material the fluorescence intensity of the competitor complex was reduced to 486 counts with a 128 ms integration time from 646 counts when no atrazine was added. This competitive assay may be used to detect the presence of atrazine at very low concentrations (30 ppm) in a starting material.

In addition, as demonstrated in FIG. 18, the fluorescence intensity of the competitor complex was inversely related to the concentration of atrazine in the starting material. When the starting material contained 30 ppm atrazine, the fluorescence intensity of the competitor complex was higher (closer to the intensity of the control containing no atrazine) than when the starting material contained 50 ppm atrazine. This dose responsiveness indicates that the competitive assay described herein may be used to quantify the amount of a contaminant in a starting material, by comparing an experimental sample containing an unknown quantity of the contaminant, atrazine in this example, to a dose curve obtained from adding known quantities of the contaminant to the experiment.

While various embodiments have been described, it will be apparent to those of ordinary skill in the art that many more embodiments and implementations are possible within the scope of the claims. Accordingly, the invention is not to be restricted except in light of the attached claims and their equivalents.

What is claimed is:

1. A system for separating a contaminant from a material that includes the contaminant, the system comprising:
   a housing;
   a chamber supported by the housing and configured to receive the material and a plurality of magnetic particles, the magnetic particles capable of binding an affinity moiety, wherein the affinity moiety is capable of binding to the contaminant;
   a controller configured to produce a first signal to mix the magnetic particles with the material, such that at least a portion of the magnetic particles binds to the contaminant, and a second signal to separate the magnetic particles and the bound contaminant from the material; and
   a magnetic field subsystem in communication with the controller and configured to create within the chamber a rotational magnetic field in response to the first signal and a fixed magnetic field in response to the second signal,
   wherein the rotational magnetic field comprises a plurality of magnetic fields which rotate in opposite directions.

2. The system of claim 1, wherein the magnetic field subsystem comprises a plurality of pairs of electromagnetic coils disposed adjacent to the chamber, the pairs of coils being arranged in layers from a top to a bottom of the chamber.

3. The system of claim 1, wherein the magnetic particles comprise magnetic nanoparticles.

4. The system of claim 1, wherein the material is selected from the group consisting of a food product, an environmental sample and a clinical sample.

5. The system of claim 4, wherein the clinical sample is selected from the group consisting of a urine sample, a blood sample, a fecal sample, a swab from the surface of the skin, a swab from the surface of an organ, and a tissue sample.

6. The system of claim 4, wherein the food product is selected from the group consisting of a fruit, a vegetable, a raw food, a ready-to-eat food, a beef product, a pork product, a poultry product, a sea food product, or a dairy product.

7. The system of claim 6, wherein the poultry product is selected from the group consisting of a chicken carcass, a chicken carcass wash water sample, a deboned chicken, a ground poultry meat sample and a poultry patty.

8. The system of claim 4, wherein the environmental sample is selected from the group consisting of a water sample, an air sample and a soil sample.

9. The system of claim 1, wherein the contaminant is selected from the group consisting of a prokaryote, a eukaryote, a virus, a polypeptide, and a chemical.

10. The system of claim 9, wherein the chemical is selected from the group consisting of a herbicide and a pesticide.

11. The system of claim 10, wherein the herbicide is 2-chloro-4-(ethylamine)-6-(isopropylamine)-s-triazine.

12. The system of claim 9, wherein the polypeptide is selected from the group consisting of a toxin and a prion.

13. The system of claim 9, wherein the prokaryote is selected from the group consisting of *Escherichia coli, Escherichia coli* O157:H7, *Salmonella* spp., and *Listeria monocytogenes*.

14. The system of claim 1, wherein the affinity moiety comprises an antibody.

15. The system of claim 1, wherein each magnetic particle is coupled to a linker capable of binding an antibody.

16. The system of claim 15, wherein the linker is selected from the group consisting of Protein A, Protein G, an Fc receptor, and an anti-Fc antibody.

17. The system of claim 16, wherein the linker comprises a bridging complex selected from the group consisting of: biotin-streptavidin, biotin-avidin, Protein A-IgG, Protein G-IgG, and IgG-anti-IgG.

* * * * *